(12) United States Patent
Banet et al.

(10) Patent No.: US 11,229,405 B2
(45) Date of Patent: *Jan. 25, 2022

(54) NECK-WORN PHYSIOLOGICAL MONITOR

(71) Applicant: toSense, Inc., La Jolla, CA (US)

(72) Inventors: Matthew Banet, San Diego, CA (US); Marshal Singh Dhillon, San Diego, CA (US); Susan Meeks Pede, Encinitas, CA (US); Kenneth Robert Hunt, Vista, CA (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 233 days.

This patent is subject to a terminal disclaimer.

(21) Appl. No.: 14/975,646

(22) Filed: Dec. 18, 2015

(65) Prior Publication Data

US 2017/0172516 A1    Jun. 22, 2017

(51) Int. Cl.
*A61B 5/00*    (2006.01)
*A61B 5/0537*    (2021.01)
(Continued)

(52) U.S. Cl.
CPC .......... *A61B 5/7275* (2013.01); *A61B 5/0002* (2013.01); *A61B 5/02* (2013.01); *A61B 5/024* (2013.01); *A61B 5/0205* (2013.01); *A61B 5/02028* (2013.01); *A61B 5/0245* (2013.01); *A61B 5/02108* (2013.01); *A61B 5/02438* (2013.01); *A61B 5/0537* (2013.01);
(Continued)

(58) Field of Classification Search
None
See application file for complete search history.

(56) References Cited

U.S. PATENT DOCUMENTS

| | | | |
|---|---|---|---|
| 2005/0190065 A1* | 9/2005 | Ronnholm | A61M 21/00 340/575 |
| 2007/0021673 A1* | 1/2007 | Arbel | A61B 5/02 600/500 |

(Continued)

OTHER PUBLICATIONS

Safe Circuit Design, Jun. 2015, All About Circuits.*
(Continued)

*Primary Examiner* — Eric F Winakur
*Assistant Examiner* — Abid A Mustansir
(74) *Attorney, Agent, or Firm* — K&L Gates LLP

(57) ABSTRACT

The invention provides a neck-worn sensor that is a single, body-worn system that measures the following parameters from an ambulatory patient: heart rate, pulse rate, pulse oximetry, respiratory rate, temperature, thoracic fluid levels, stroke volume, cardiac output, and a parameter sensitive to blood pressure called pulse transit time. From stroke volume, a first algorithm employing a linear model can estimate the patient's pulse pressure. And from pulse pressure and pulse transit time, a second algorithm, also employing a linear algorithm, can estimate systolic blood pressure and diastolic blood pressure. Thus, the sensor can measure all five vital signs along with hemodynamic parameters. It also includes a motion-detecting accelerometer, from which it can determine motion-related parameters such as posture, degree of motion, activity level, respiratory-induced heaving of the chest, and falls.

18 Claims, 19 Drawing Sheets

(51) Int. Cl.
   A61B 5/024      (2006.01)
   A61B 5/0245     (2006.01)
   G16H 40/67      (2018.01)
   A61B 5/25       (2021.01)
   A61B 5/282      (2021.01)
   A61B 5/318      (2021.01)
   A61B 5/02       (2006.01)
   A61B 5/021      (2006.01)
   A61B 5/08       (2006.01)
   A61B 5/1455     (2006.01)
   A61B 5/0205     (2006.01)
   G16H 50/30      (2018.01)

(52) U.S. Cl.
   CPC ............. *A61B 5/08* (2013.01); *A61B 5/0816* (2013.01); *A61B 5/14551* (2013.01); *A61B 5/25* (2021.01); *A61B 5/282* (2021.01); *A61B 5/318* (2021.01); *A61B 5/6822* (2013.01); *G16H 40/67* (2018.01); *A61B 5/0022* (2013.01); *A61B 5/7225* (2013.01); *A61B 2560/0468* (2013.01); *G16H 50/30* (2018.01)

(56) References Cited

U.S. PATENT DOCUMENTS

| | | | | |
|---|---|---|---|---|
| 2008/0114220 A1* | 5/2008 | Banet | ................ | A61B 5/14551 |
| | | | | 600/301 |
| 2010/0268056 A1* | 10/2010 | Picard | .................. | A61B 5/0531 |
| | | | | 600/388 |
| 2011/0021941 A1* | 1/2011 | Watson | ................ | A61B 5/0816 |
| | | | | 600/529 |
| 2011/0066062 A1 | 3/2011 | Banet et al. | | |
| 2013/0289424 A1* | 10/2013 | Brockway | ............ | A61B 5/0402 |
| | | | | 600/509 |
| 2014/0024958 A1* | 1/2014 | Seppa | .................. | A61B 5/0452 |
| | | | | 600/529 |
| 2014/0128757 A1* | 5/2014 | Banet | ..................... | A61B 5/053 |
| | | | | 600/513 |
| 2014/0187897 A1* | 7/2014 | Banet | ................ | A61B 5/02055 |
| | | | | 600/382 |
| 2014/0236031 A1* | 8/2014 | Banet | ................... | A61B 5/6831 |
| | | | | 600/513 |
| 2014/0330090 A1* | 11/2014 | Banet | ................... | A61B 5/6822 |
| | | | | 600/301 |
| 2017/0143216 A1* | 5/2017 | Oksala | ............ | A61B 5/02125 |
| 2017/0172423 A1* | 6/2017 | Banet | ................... | A61B 5/0205 |
| 2017/0172427 A1* | 6/2017 | Banet | ....................... | A61B 5/02 |
| 2017/0172428 A1* | 6/2017 | Banet | ................ | A61B 5/02108 |

OTHER PUBLICATIONS

Anand et al., Monitoring Changes in Fluid Status With a Wireless Multisensor Monitor: Results From the Fluid Removal During Adherent Renal Monitoring (FARM) Study. Congest Heart Fail. 2012;18:32-36.

Bernstein, Impedance Cardiography, Pulsatile blood flow and the biophysical and electrodynamic basis for the stroke volume equations., J Elect Bioimpedance. 2010;1:2-17.

Harley et al., Pressure-Flow Studies in Man. An Evaluation of the Duration of the Phases of Systole. J Clin Invest. 1969;48:895-905.

Jacques et al., Pulse pressure variation and stroke volume variation during increased intra-abdominal pressure: an experimental study. Crit Care. 2011;15(1):R33.

Packer et al., Utility of Impedance Cardiography for the Identification of Short-Term Risk of Clinical Decompensation in Stable Patients With Chronic Heart Failure. J Am Coll Cardiol. Jun. 6, 2006;47(11):2245-2252.

* cited by examiner

ECG → Heart Rate, Heart Rate Variability

TBI – DC → Thoracic Fluid Level

TBI – AC

TBI – AC LP Filtered → Respiration Rate, Apnea

TBI – AC BP Filtered → Stroke Volume, Cardiac Output

NECK-WORN PHYSIOLOGICAL MONITOR

FIELD OF THE INVENTION

The invention relates to sensors that measure physiological signals from patients and the use of such sensors.

BACKGROUND OF THE INVENTION

There are a number of physiological parameters that can be assessed by measuring physiological or physiologically influenced electrical signals from a patient. Some signals, such as thoracic bioimpedance (TBI) and electrocardiogram (ECG) waveforms, are measured with electrodes that attach to the patient's skin. Processing of these waveforms yields parameters such as heart rate (HR), respiration rate (RR), heart rate variability (HRV), stroke volume (SV), cardiac output (CO), and parameters related to thoracic fluids, e.g. thoracic fluid content (TFC). Certain physiological conditions can be identified from these parameters when they are obtained at a single point in time; others require assessment over some period of time to identify trends in the parameters. In both cases, it is important to obtain the parameters consistently and with high repeatability and accuracy.

Some conditions require measuring parameters over a relatively short or modest period of time. For example, Holter monitors can characterize various types of cardiac arrhythmias by measuring HR, HRV, and ECG waveforms over a 24 to 48-hour period of time. On the other hand, chronic diseases such as congestive heart failure (CHF) and end-stage renal disease (ESRD) can require periodic measurements of fluids and weight throughout the patient's life. Not surprisingly, patient compliance typically decreases as the measurement period increases. This is particularly true when measurements are made outside of a conventional medical facility, e.g., at the patient's home or in a residential facility such as a nursing home.

Measuring some physiological parameters does not require a high degree of precision and/or consistency in the body location at which a measurement is taken. For example, measuring a patient's temperature is frequently performed with an oral thermometer that is simply placed somewhere under the tongue. Here, the exact placement of the thermometer does not have a big impact on the measured temperature value. Likewise, parameters that depend on time-dependent features in waveforms, such as HR, which depends on the time-dependent variation of R-R intervals in the ECG waveforms, are relatively insensitive to sensor positioning. In this case, the R-R intervals show almost no variation with positioning of electrodes on the patient's thoracic cavity. Blood pressure, in contrast, shows some sensitivity to measurement location. When measured with a sphygmomanometer, the blood pressure value is relatively insensitive to the general alignment of the cuff over the brachial artery, but will vary when measured at other locations on the body, such as the wrist, thigh, or even the opposing arm. On the contrary, measuring amplitude-dependent features in waveforms, such as TFC, will be strongly dependent on the positioning of electrodes. In this case, the value of TFC depends strongly on the impedance between the electrodes, and this in turn will vary with the electrodes' placement. Here, deviation in day-to-day placement of electrodes can result in measurement errors, particularly when trends of the measured parameters are extracted. This, in turn, can lead to misinformation, nullify the value of such measurements, and thus negatively impact treatment.

Known Devices and Relevant Physiology

Medical devices that measure time-dependent ECG and TBI waveforms from patients typically connect through cables or lead wires to disposable electrodes adhered at various locations on a patient's body. Analog circuits within a given device, which are typically located remote from the patient's body in the device, process the signals to generate the waveforms. With further analysis, such waveforms yield parameters such as HR, TFC, SV, CO, and RR. Other systems within a given medical device might measure vital signs such as pulse oximetry (SpO2), pulse rate (PR), systolic (SYS) and diastolic (DIA) blood pressure, and temperature (TEMP).

Disposable electrodes that measure ECG and TBI waveforms are typically worn on the patient's chest or legs and include: i) a conductive hydrogel that contacts the patient; ii) a Ag/AgCl-coated eyelet that contacts the hydrogel; iii) a conductive metal post that connects to a lead wire or cable extending from the device; and iv) an adhesive backing that adheres the electrode to the patient. Unfortunately, during a measurement, the lead wires can pull on the electrodes if the device is moved relative to the patient's body, or if the patient ambulates and snags the lead wires on various objects. Such pulling can be uncomfortable or even painful, particularly where the electrodes are attached to hirsute parts of the body, which can inhibit patient compliance with long-term monitoring. Moreover, such pulling can degrade or even completely eliminate adhesion of the electrodes to the patient's skin, thereby degrading or completely destroying the ability of the electrodes to sense the physiolectrical signals at various electrode locations.

Some devices that measure ECG and TBI waveforms are worn entirely on the patient's body. These devices have been improved to feature simple, patch-type systems that include both analog and digital electronics connected directly to underlying electrodes. Such devices are typically prescribed for relatively short periods of time, e.g. for a time period ranging from a few days to several weeks. They are typically wireless, and include technologies such as Bluetooth® transceivers to transmit information over a short range to a second device, which then includes a cellular radio to transmit the information to a web-based system.

Measurement of SpO2 values is almost always done from the patient's fingers, earlobes, or in some cases toes. In these cases, patients wear an optical sensor to measure photoplethysmogram (PPG) waveforms, which are then processed to yield SpO2 and PR. TEMP is typically measured with a thermometer inserted in the patient's mouth.

Assessing TFC, weight, and hydration status is important in the diagnosis and management of many diseases. For example, ESRD occurs when a patient's kidneys are no longer able to work at a level needed for day-to-day life. The disease is most commonly caused by diabetes and high blood pressure, and is characterized by swings in SYS and DIA along with a gradual increase in fluids throughout the body. Patients suffering from ESRD typically require hemodialysis or ultrafiltration to remove excess fluids. Thus to characterize ESRD, accurate measurement of these TFC can eliminate the need for empirical clinical estimations that often lead to over-removal or under-removal of fluid during dialysis, thereby preventing hemodynamic instability and hypotensive episodes (Anand et al., "*Monitoring Changes in Fluid Status With a Wireless Multisensor Monitor: Results From the Fluid Removal During Adherent Renal Monitoring (FARM) Study*," Congest Heart Fail. 2012; 18:32-36). A similar situation exists with respect to CHF, which is a complicated disease typically monitored using a "constellation" of physiological factors, i.e., fluid status (e.g. TFC), vital signs (i.e. HR, RR, TEMP, SYS, DIA, and SpO2), and hemodynamic parameters (e.g. CO, SV). Accurate measurement of these parameters can aid in managing patients, particularly for dispersing diuretic medications, thereby reducing expensive hospital readmissions (Packer et al., "*Utility of Impedance Cardiography for the Identification of Short-Term Risk of Clinical Decompensation in Stable Patients With Chronic Heart Failure*," J Am Coll Cardiol 2006; 47:2245-52).

CHF is a particular type of heart failure (HF), which is a chronic disease driven by complex pathophysiology. In general terms, this condition occurs when SV and CO are insufficient in adequately perfusing the kidneys and lungs. Causes of this disease are well known and typically include coronary heart disease, diabetes, hypertension, obesity, smoking, and valvular heart disease. In systolic HF, ejection fraction (EF) can be diminished (<50%), whereas in diastolic HF this parameter is typically normal (>65%). The common signifying characteristic of both forms of heart failure is time-dependent elevation of the pressure within the left atrium at the end of its contraction cycle, or left ventricular end-diastolic pressure (LVEDP). Chronic elevation of LVEDP causes transudation of fluid from the pulmonary veins into the lungs, resulting in shortness of breath (dyspnea), rapid breathing (tachypnea), and fatigue with exertion due to the mismatch of oxygen delivery and oxygen demand throughout the body. Thus, early compensatory mechanisms for HF that can be detected fairly easily include increased RR and HR.

As CO is compromised, the kidneys respond with decreased filtration capabilities, thus driving retention of sodium and water, and leading to an increase in intravascular volume. As the LVEDP rises, pulmonary venous congestion worsens. Body weight increases incrementally, and fluids may shift into the lower extremities. Medications for HF are designed to interrupt the kidneys' hormonal responses to diminished perfusion, and they also work to help excrete excess sodium and water from the body. However, an extremely delicate balance between these two biological treatment modalities needs to be maintained, since an increase in blood pressure (which relates to afterload) or fluid retention (which relates to preload), or a significant change in heart rate due to a tachyarrhythmia, can lead to decompensated HF. Unfortunately, this condition is often unresponsive to oral medications. In that situation, admission to a hospital is often necessary for intravenous diuretic therapy.

In medical centers, HF is typically detected using Doppler/ultrasound, which measures parameters such as SV, CO, and EF. In the home environment, on the other hand, gradual weight gain measured with a simple weight scale is one method to indicate CHF. However, this parameter is typically not sensitive enough to detect the early onset of CHF—a particularly important time when the condition may be ameliorated by a change in medication or diet.

SV is the mathematical difference between left ventricular end-diastolic volume (EDV) and end-systolic volume (ESV) and represents the volume of blood ejected by the left ventricle with each heartbeat; a typical value is about 70-100 mL. EF relates to EDV and ESV as described below in Equation 1:

$$EF = \frac{SV}{EDV} = \frac{EDV - ESV}{EDV} \quad (1)$$

CO is the average, time-dependent volume of blood ejected from the left ventricle into the aorta and, informally, indicates how efficiently a patient's heart pumps blood through their arterial tree; a typical value is about 5-7 L/min. CO is the product of HR and SV, i.e., $$CO = SV \times HR \quad (2)$$

CHF patients, and in particular those suffering from systolic HF, may receive implanted devices such as pacemakers and/or implantable cardioverter-defibrillators to increase EF and subsequent blood flow throughout the body. These devices may include circuitry and algorithms to measure the electrical impedance between different leads of the device. As thoracic fluid increases in the CHF patient, the impedance typically is reduced. Thus, this parameter, when read by an interrogating device placed outside the patient's body, can indicate the onset of heart failure.

Monitoring Solutions

As illustrated in FIG. 1, many of the above-mentioned parameters can be used as early markers of the onset of CHF. EF is typically low in patients suffering from this chronic disease, and can be further diminished by factors such as a change in physiology, an increase in sodium in the patient's diet, or non-compliance with medications. This is manifested by a gradual decrease in SV, CO, and SYS that typically occurs between two and three weeks before a hospitalization event. The reduction in SV and CO diminishes perfusion to the kidneys. As described above, these organs then respond with a decrease in their filtering capacity, thus causing the patient to retain sodium and water and leading to an increase in intravascular volume. This, in turn, leads to congestion, which is manifested to some extent by a build-up of fluids in the patient's thoracic cavity (e.g. TFC). Typically, a detectable increase in TFC occurs about 1-2 weeks before hospitalization becomes necessary. Body weight increases after this event, typically by between three and five pounds, causing fluids to shift into the lower extremities. At this point, the patient may experience an increase in both HR and RR to increase perfusion. Nausea, dyspnea, and weight gain typically grow more pronounced a few days before hospitalization becomes necessary. As noted above, a characteristic of decompensated HF is that it is often unresponsive to oral medications; thus, at this point, intravenous diuretic therapy in a hospital setting often becomes mandatory. A hospital stay for intravenous diuretic therapy typically lasts about 4 days, after which the patient is discharged and the cycle shown in FIG. 1 can start over once more.

Not only is such cyclical pathology and treatment physically taxing on the patient, it is economically taxing on society as well. In this regard, CHF and ESRD affect, respectively, about 5.3 million and 3 million Americans, resulting in annual healthcare costs estimated at $45 billion for CHF and $35 billion for ESRD. CHF patients account for approximately 43% of annual Medicare expenditures, which is more than the combined expenditures for all types of cancer. Somewhat disconcertingly, roughly $17 billion of this is attributed to hospital readmissions. CHF is also the leading cause of mortality for patients with ESRD, and this demographic costs Medicare nearly $90,000/patient annually. Thus, there understandably exists a profound financial incentive to keep patients suffering from these diseases out of the hospital. Starting in 2012, U.S. hospitals have been penalized for above-normal readmission rates. Currently, the penalty has a cap of 1% of payments, growing to over 3% in the next three years.

Of some promise, however, is the fact that CHF-related hospital readmissions can be reduced when clinicians have access to detailed information that allows them to remotely titrate medications, monitor diet, and promote exercise. In fact, Medicare has estimated that 75% of all patients with ESRD and/or CHF could potentially avoid hospital readmissions if treated by simple, effective programs.

Thus, with the aim of identifying precursors to conditions such as CHF and ESRD, physicians can prescribe monitoring solutions to patients living at home. Typically such solutions include multiple, standard medical devices, e.g. blood pressure cuffs, weight scales, and pulse oximeters. In certain cases, patients use these devices daily and in a sequential manner, i.e. one device at a time. The patient then calls a central call center to relay their measured parameters. In more advanced systems, the devices are still used in a sequential manner, but automatically connect through a short-range wireless link (e.g. Bluetooth®) to a "hub", which then forwards the information off to a call center. Often the hub features a simple user interface that poses basic questions to the patient, e.g. questions concerning their diet, how they are feeling, and whether or not medications were taken.

Patients can also wear ambulatory cardiac monitors for periods of time ranging from several days to weeks to characterize cardiac conditions, such as arrhythmias. Such devices are called Holter or event monitors, and measure parameters such as HR, HRV, and ECG waveforms. They typically include a collection of chest-worn ECG electrodes (typically 3 or 5); an ECG circuit that collects analog signals from the ECG electrodes and converts them into multi-lead ECG waveforms; and a processing unit that analyzes the ECG waveforms to determine cardiac information. Typically, the patient wears the entire system on their body, but such systems can be awkward, cumbersome, and/or uncomfortable, e.g., due to the electrodes pulling the patient's skin/hair. Some ambulatory systems may simply include on-board memory that stores information for retrieval at a later time, at which point the information is analyzed to generate a report describing the patient's cardiac rhythm. More modern systems include wireless capabilities to transmit ECG waveforms and other numerical data through a cellular interface to an Internet-based system, where the report is generated using automated algorithms. In most cases, the report is imported into the patient's electronic medical record (EMR), which avails the report to cardiologists or other clinicians who can then use it to help characterize and treat the patient.

In order for such monitoring to be therapeutically effective, however, it is important for the patient to use their equipment consistently, both in terms of the duration and manner in which it is used. Less-than-satisfactory consistency with the use of any medical device (in terms of duration and/or methodology) may be particularly likely in an environment such as the patient's home or a nursing home, where direct supervision may be less than optimal.

SUMMARY OF THE INVENTION

In view of the foregoing, it would be beneficial to improve patient compliance with at-home monitoring. Here, compliance indicates the regularity and manner in which a patient uses a device. A sensor according to the invention, which facilitates monitoring a patient for HF, CHF, ESRD, cardiac arrhythmias, and other diseases in both home and clinical environments, could achieve this goal. The sensor is worn like a conventional necklace, comfortably around the neck, and features a mechanical mechanism that ensures consistent placement when used on a daily basis, thereby improving the repeatability and reproducibility of its measurements. Additionally, the sensor makes simultaneous measurements of multiple parameters, and thus obviates the need to use multiple devices. Both of these features may improve patient compliance.

The sensor is able to detect the early onset of these and other diseases, thereby providing clinicians information that, when acted on, may prevent hospitalization. More particularly, the invention features a neck-worn sensor that is an integrated, body-worn system, which measures the following parameters from a patient: HR, PR, SpO2, RR, TEMP, a thoracic fluid index (TFI), SV, CO, and a parameter sensitive to blood pressure called pulse transit time (PTT). From SV, a first algorithm employing a linear model can estimate the patient's pulse pressure (PP). And from PP and PTT, a second algorithm, also employing a linear algorithm, can estimate SYS and DIA. Thus, the sensor, acting alone, can measure all five vital signs (HR/PR, SpO2, RR, TEMP, and SYS/DIA) along with hemodynamic parameters (SV, CO, TFI). Trends in some of these parameters, e.g. SV, SYS, and TFI, may predict the onset of HF (e.g. CHF) before its severity is such that the patient requires admission to a hospital. By measuring this constellation of properties in the patient's home and then wirelessly transmitting them to a clinician for evaluation, the sensor facilitates timely medical intervention that may ultimately keep the patient out of the hospital.

The sensor also includes a motion-detecting accelerometer, from which it can determine motion-related parameters such as posture, degree of motion, activity level, respiratory-induced heaving of the chest, and falls. The sensor can operate additional algorithms to process the motion-related parameters to measure vital signs and hemodynamic parameters when motion is minimized and below a pre-determined threshold, thereby reducing artifacts. Moreover, the sensor estimates motion-related parameters such as posture to improve the accuracy of calculations for vital signs and hemodynamic parameters.

Disposable electrodes attach directly to the sensor to secure it in close proximity to the patient's body without bothersome cables. In particular, the electrodes are provided in patches, with each electrode patch containing two electrode regions to measure ECG and TBI waveforms. The patches easily and releasably connect to circuit boards contained within the sensor by means of magnets that are electrically connected to the circuit boards to provide signal-conducting electrical couplings. Prior to use, the electrodes are simply held near the circuit boards, and magnetic attraction causes the electrode patches to snap into proper position, thereby ensuring proper positioning of the electrodes on the patient's body.

Using light-emitting diodes operating in the red (e.g. 600 nm) and infrared (e.g. 800 nm) spectral regions, the sensor measures SpO2 and PR by pressing lightly against capillary beds in the patient's chest. Operating in a reflection-mode geometry, the sensor measures PPG waveforms with both red and infrared wavelengths. SpO2 is processed from alternating and static components of these waveforms. PR, in turn, can be calculated from neighboring pulses, typically from the PPG waveform generated with infrared light, as this typically has a relatively high signal-to-noise ratio.

All analog and digital electronics associated with these various measurements are directly integrated into the sensor. This means that a single, unobtrusive component—shaped like a piece of conventional jewelry instead of a bulky medical device—measures a robust set of parameters that can characterize a patient using both one-time and continuous measurements. Measurements can take place over just a few minutes or several hours, and can be made in medical facilities and at home. The sensor includes a simple LED in its base (i.e. sensing) portion, which is located near the center of the chest when worn by the patient. The sensor also includes a wireless transmitter (operating Bluetooth® and/or 802.11a/b/g/n) than sends data to, e.g., a conventional mobile device (e.g. cellular telephone, tablet computer, desktop/laptop computer, or plug-in hub).

The sensor measures all of the above-mentioned properties while featuring a comfortable, easy-to-wear form factor that resembles a piece of conventional jewelry. It is lightweight (about 100 grams) and battery-powered. During use, it simply drapes around the neck, where the disposable electrodes hold it in place, as described in more detail below. Flexible, conductive elements resembling strands in a conventional necklace power on the sensor, hold it in place, and also ensure that it is consistently positioned when used on a daily basis. Moreover, the patient's neck is a location that is unobtrusive, comfortable, removed from the hands, and able to bear the weight of the sensor without being noticeable to the patient. The neck and thoracic cavity are also relatively free of motion compared to appendages such as the hands and fingers, and thus a sensor affixed to the neck region minimizes motion-related artifacts. Moreover, such artifacts are compensated for, to some degree, by the accelerometer within the sensor. And because the sensor resembles jewelry (e.g., a necklace) and is therefore considerably less noticeable or obtrusive than various prior-art devices, emotional discomfort over wearing a medical device over an extended period of time is reduced, thereby fostering long-term patient compliance with a monitoring regimen.

The sensor's form factor is designed for comfort and ease of use, with the ultimate goal of improving patient compliance so that the above-mentioned parameters can be measured in a continuous manner and on a day-to-day basis. The system is targeted for elderly, at-home patients, e.g. those suffering from chronic conditions such as HF, CHF, ESRD and related cardiac diseases, diseases of the kidneys, diabetes, and chronic obstructive pulmonary disease (COPD).

Thus, in one aspect, the invention features a sensor for simultaneously measuring SYS, SV, and TFI from a patient. The sensor features a sensing portion having a flexible housing, and an elongated securement member that extends from the sensing portion to pass around the patient's neck. The elongated securement member has sufficient length to support the sensing portion generally against the sternal portion of the patient's chest when the sensor is in use and operating. It is configured to position the sensing portion in a consistent location on the patient's body, thus optimizing the repeatability and reproducibility of each measurement. As described above, this is particularly important when trends are extracted from parameters measured on a daily basis.

The sensor features at least one pair of electrode contact points disposed within the housing, with each pair of electrode contact points comprising a current-injecting electrode contact point and a voltage-sensing electrode contact point. Also disposed within the housing is an analog ECG circuit in contact with at least one pair of electrode contact points and configured to generate an analog ECG waveform based on a sensed voltage. An analog impedance circuit, also disposed within the housing and in electrical contact with at least one pair of electrode contact points, is configured to generate an analog impedance waveform based on the sensed voltage. During a measurement, the waveforms pass to a digital processing system featuring a microprocessor and analog-to-digital converter. This system digitizes the analog ECG and TBI waveforms to generate, respectively, digital ECG and TBI waveforms.

Within the housing are systems for monitoring blood pressure (e.g. SYS), SV, and TFI. Each system features an algorithm that processes at least one of the ECG and TBI waveforms to arrive at these values. For example, the blood pressure-monitoring system uses a first algorithm to collectively process the digital TBI and ECG waveforms to determine a value of SYS. The SV-monitoring system uses a second algorithm to process the digital TBI waveform to determine a value of SV. And the TFI-measuring system uses a third algorithm to process the digital impedance waveform to determine a value of TFI.

In embodiments, the elongated securement member features a battery, conductive wires for supplying voltage and ground to the sensing component, and a clasp assembly at its distal end. During a measurement, the clasp assembly powers on the sensing component when it is attached to the sensing component. Here, the sensing component includes a circuit that prevents power from being supplied to the sensing component when the clasp assembly and sensing component are detached. The circuit, e.g., may be a control system that is configured to control the supply of electrical power from a battery, whereby electrical power is supplied to the analog and digital circuitry when the clasp assembly is mated to the second end region of the housing. In embodiments, the clasp assembly includes a first connector, the sensing component includes a second connector, and the clasp assembly powers on the sensing component when the first connector connects to the second connector. The connectors, e.g., can be magnets. These can be positioned and arranged to releasably hold the clasp assembly to the housing by way of magnetic attraction. Furthermore, an electrical circuit is completed when the magnets contact each other, which allows electrical current to flow through the sensor system so as to power circuitry within the sensor to perform the measurements described above.

In another aspect, the invention features a sensor for measuring trends in SYS, SV, and TFI measured at different times by the sensing portion. Here, the elongated securement member positions the sensing portion in roughly the same location on the patient's body to improve the repeatability and reproducibility of repeated measurements. In another aspect, the invention features a sensor for generating alerts indicating an onset of heart failure by measuring trends in SYS, SV, and TFI when each of these parameters trends to a lower value.

And in yet another aspect, the invention features a system for measuring physiological signals from a patient that includes a flexible housing, configured to be worn around a patient's neck, that includes a first component enclosing a first circuit board, a second component enclosing a second circuit board, a third component enclosing a third circuit board, a fourth component enclosing a first electrical conductor, and a fifth component enclosing a second electrical conductor. A sensor with this configuration is ideal for conforming to the contours present on the thoracic region of some patients. At least one of the first, second, and third circuit boards features either an analog circuit configured to measure at least one time-dependent analog waveform from the patient, or a digital processing system featuring a microprocessor and an analog-to-digital converter that digitizes at least one time-dependent analog waveform to generate a time-dependent digital waveform. One of the circuit boards also includes a sensor for monitoring the physiological signal from the patient. It operates an algorithm to process the time-dependent digital waveform to determine the physiological signal.

In specific embodiments of the invention, an algorithm collectively processes the digital ECG and TBI waveforms to measure SYS from a pulse transit time (PTT). Here, the algorithm: 1) processes the digital ECG waveform to determine a first time point; 2) processes the digital TBI waveform to determine a second time point; 3) analyzes the first and second time points to determine PTT; and 4) analyzes the PTT to determine a value of SYS. In embodiments, the algorithm may also: 1) process SV to determine PP; and 2) process PTT and PP to determine SYS and DIA. An algorithm may also process the digital TBI waveform to: 1) extract an amplitude of a derivatized value of the TBI waveform's AC component; 2) extract an amplitude of the TBI waveform's DC component; 3) extract an estimated injection time; and 4) collectively process the amplitudes of the AC and DC components, along with the injection time, to determine SV. Furthermore, the amplitude of a DC component of the digital TBI waveform may be processed to determine the value of TFI.

In alternate embodiments, the sensor can calculate a parameter called vascular transit time (VTT) from fiducial points (e.g. the base or maximum value of the derivatized waveform) of each pulsatile component contained in both the PPG and TBI waveforms. VTT can then be used in place of PTT to calculate SYS. This approach has certain advantages, namely in that VTT lacks certain time components related to the cardiac cycle—called 'systolic time intervals—that do not depend on blood pressure. Inclusion of such components may thus add errors to the blood pressure measurement. Examples of such systolic time intervals are pre-injection period (PEP) and the isovolumetric contraction time (ICT).

In still other embodiments, the sensor or the web-based system can calculate a time-dependent change or deviation in any of the above-mentioned parameters (e.g. SV, CO, SYS, DIA, TFI) to predict the onset of a disease, e.g. CHF.

In specific embodiments of sensors according to any of these aspects of the invention, flexibility is imparted to the sensing portion of the sensor, so that it can conform to the individual curvatures of different patients' chests, by forming the housing in two or more segments, which are connected to each other by flexible connector segments. Rigid circuit boards located within the various housing segments are connected to each other via flexible circuits, which pass through the flexible connector segments.

BRIEF DESCRIPTION OF THE DRAWINGS

Embodiments of the invention will now be described in greater detail in conjunction with the figures, in which:

FIG. 11A) ECG waveform; FIG. 11B) DC components of the TBI waveform; FIG. 11C) unfiltered AC components of the TBI waveform; FIG. 11D) low pass-filtered AC components of the TBI waveform; and FIG. 11E) band pass-filtered AC components of the TBI waveform;

FIG. 12A) ECG and derivatized TBI waveforms; and FIG. 12B) low-passed filtered AC components of the TBI waveform;

DETAILED DESCRIPTION

Remote Patient-Monitoring System

Figure 1:
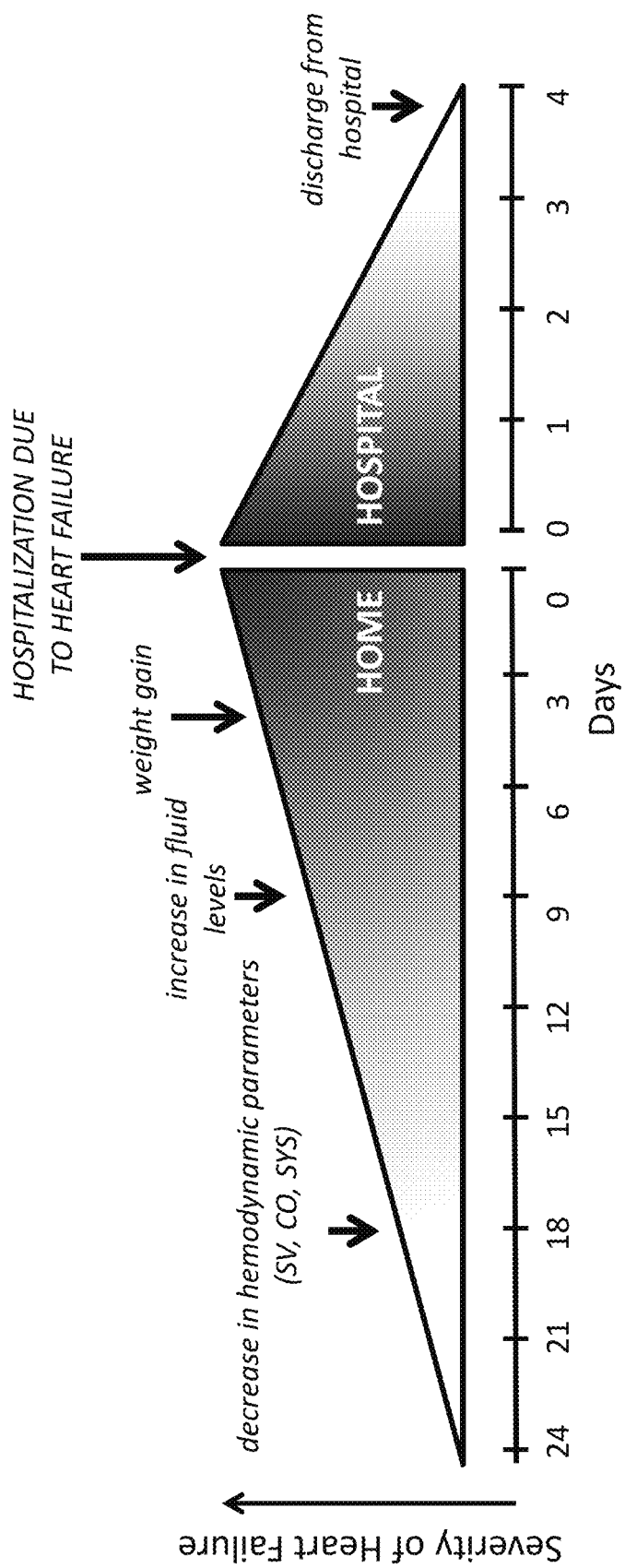
FIG. 1 is a timeline illustrating how detectable physiological parameters precede and can be used to predict the onset of CHF.
Figure 2:
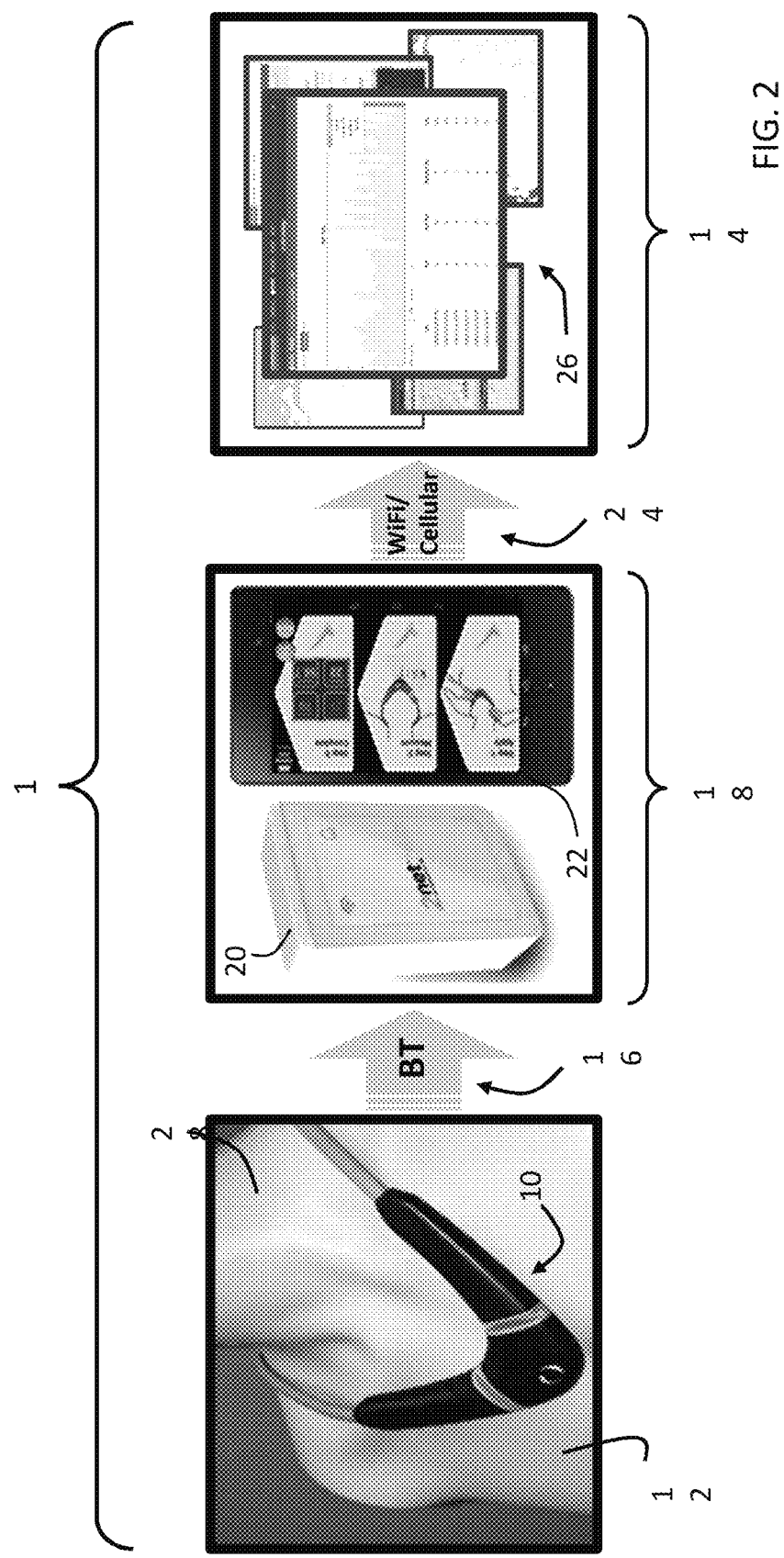
FIG. 2 is a schematic diagram illustrating the use of a neck-worn sensor according to the invention as part of a system for remote monitoring of patients.

As illustrated in FIG. 2, a sensor 10 according to the invention is one component of an overall system 1 designed to facilitate remote monitoring of—and, if required, therapeutic intervention on behalf of—a patient 12. As will be explained in greater detail below, the sensor 10 measures numerical and waveform data, and then sends this wirelessly to a gateway system 18, and from there to a web-based system 26 that can be viewed at a remote facility 14 such as a hospital, medical clinic, nursing facility, and/or eldercare facility. There, clinicians can evaluate or further process the data to evaluate the patient 12.

In particular, after measuring and processing the patient's physiological parameters as addressed below, the sensor 10 automatically transmits data through an internal Bluetooth® wireless transmitter (identified schematically at 16) to a gateway system 18, which suitably may be either a 2Net™ system 20 available from Qualcomm, Inc. or a tablet computer or other handheld device 22 running a customized graphical user interface (GUI). Either type of gateway 18 (i.e., a 2Net™ system 20 or a tablet computer/handheld device 22) preferably runs a downloadable software application that accesses the gateway's internal Bluetooth® driver. The 2Net™ system 20 lacks any display, but features a series of LEDs that indicate when it receives and then transmits information for further review. The GUI on the tablet computer/handheld device 22 renders data on the device's screen, and also guides a patient through the measurement process. Both gateway devices use internal WiFi and/or cellular transmission channels 24 to transmit data to an IP address associated with the web-based system 26, which is typically operated at the remote facility 14. The web-based system 26 displays data from multiple patients for clinicians, and may also include an interface for individual patients. For example, the web-based system 26 may display ECG and TBI waveforms; trended numerical data; and the patient's medical history and demographic information. A clinician viewing the web-based system 26 may, for example, analyze the data and then call the patient 12 to have him or her adjust his/her medications and/or diet.

Alternatively, the sensor 10 can automatically transmit data via Bluetooth® transmitter to a personal computer (not illustrated), which then uses a wired or wireless Internet connection to transmit data to the web-based system 26. In such a configuration, the personal computer runs a software program configured to download data from the sensor 10; to display the data for the patient 12 in an easy-to-understand format; and to forward the data to the computer server that runs the web-based system 26 for relatively complex analysis as described below. In yet another configuration, the sensor 10 can connect to the personal computer via a USB connection, and download and forward data to the web-based system 26 using a wired Ethernet connection, as described above.

Basic Construction of Sensor

FIGS. 3-10 show embodiments of a sensor 10 according to the invention designed to be worn by a patient 12. The sensor 10 is typically worn around the patient's neck 28 so that it rests against their sternum, similar to a necklace or other neck-adorning jewelry. The sensor 10 features a sensing portion 30 and a securement member 32 (or securement members in an alternate embodiment, not illustrated). As illustrated, the securement member 32 extends from a first end 34 of the sensing portion 30 and attaches to a second end 36 of the sensing portion 30. The securement member 32 is long enough to pass behind the patient's neck 28 and to hold the sensing portion 30 in proper position for sensing electrodes attached to its rear, patient-facing surface to be attached to the proper locations on the patient's chest. This ensures that the sensing portion 30 is placed in approximately the same position for each measurement made on a particular patient, and that it is held in proper position to acquire the relevant bioelectric signals, as explained more fully below. Additionally, the securement member 32 houses a battery in battery compartment 38, which is positioned generally in the middle of the securement member 32 (lengthwise speaking) such that it is positioned inconspicuously behind the patient's neck 28 when the sensor 10 is worn.

In other, non-illustrated embodiments, the securement member could be split in the middle, with flexible yet shape-retaining "branches" extending from the first and second ends 34, 36 of the sensing portion 30 so as to pass behind the patient's neck 28, but not connect, much like a physician's stethoscope. In that case, the battery compartment could be located in one of the branches or, alternatively, in the sensing portion 30 of the sensor 10. In still further non-illustrated embodiments, a securement member might not be included, in which case attachment of the electrodes to the patient's body would, by itself, be used to hold the sensor in position. Ultimately, however, where a securement member is provided to facilitate positioning of the sensing portion 30 on the patients' body, what is important is simply that the securement member should be configured to pass at least substantially around the patient's neck 28 (which includes a configuration in which lateral halves of the securement member pass posteriorly over the trapezius muscles without curving medially toward the spine). In other words, the securement member 32 passes sufficiently over the trapezius region and/or behind the neck to support the sensing portion 30 and prevent it from falling before the sensing portion 30 is secured to the patient's body via the electrodes, as described more fully below.

The sensing portion 30 is constructed in two or more sections or segments, e.g. a central segment 42 and two outboard segments 40a and 40b, to the rear of which electrode patches are attached as described below. The segments are connected to each other by means of flexible conductor segments 56a, 56b, which in turn are encased in flexible housing 46 and 48. The flexible conductor segments 56a, 56b are typically made from a polymeric material, e.g. Kapton® flexible printed circuits available from the DuPont Corporation. Such materials are essentially a flexible, polymeric film that encases one or more thin conducting members, which are typically made from copper. Each of the segments 40a, 40b, and 42 includes, respectively, a rigid circuit board 52a, 52b, and 54 (best shown in FIG. 5) populated with discrete electrical circuit components, described in more detail below. The rigid circuit boards 52a, 52b, and 54 connect to one another via the flexible conductor segments 56a, 56b, which each include 20 conductive members.

Figure 3A:
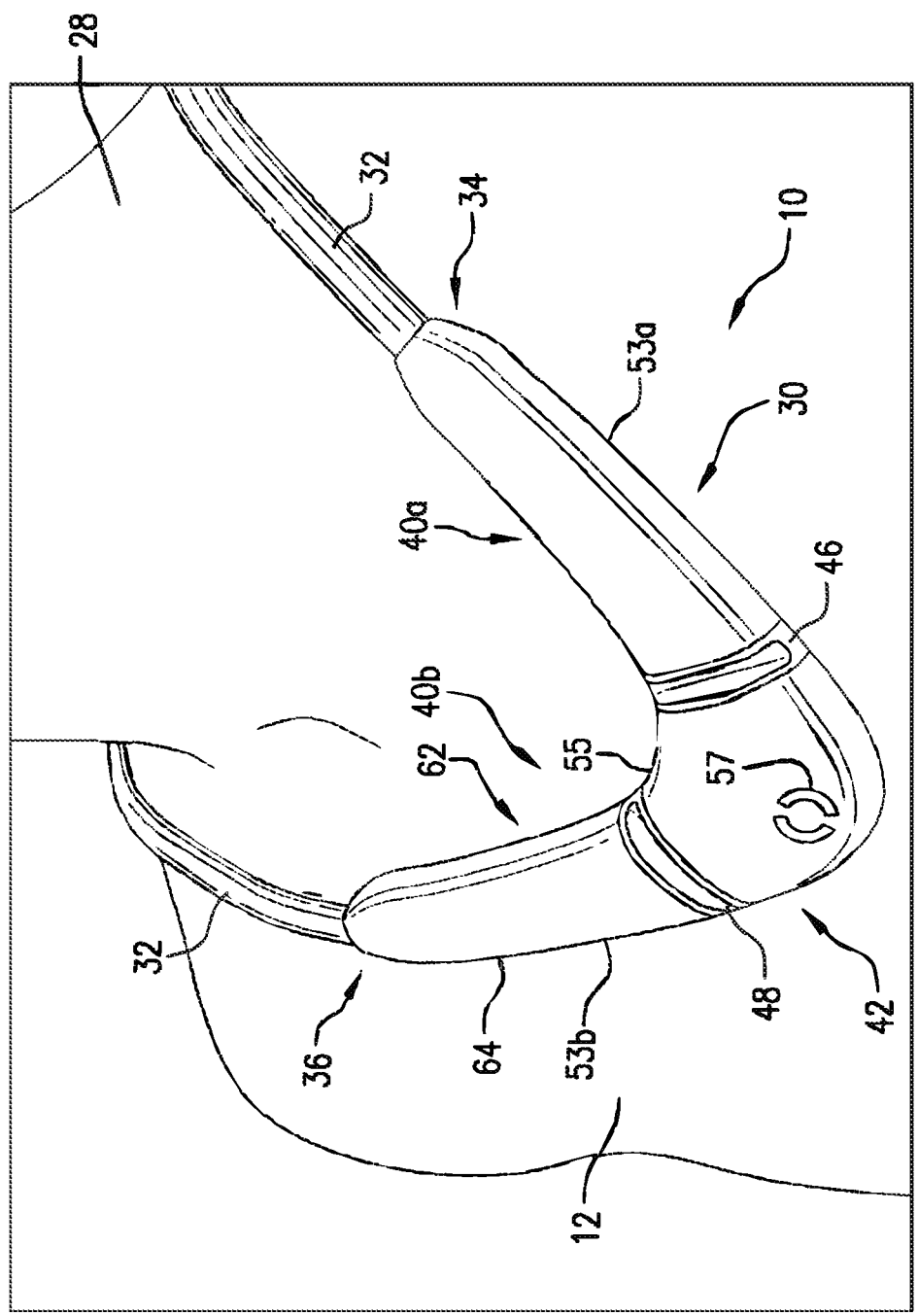
FIG. 3A is a photograph of an embodiment of a neck-worn sensor according to the invention, as illustrated in use in FIG. 2, with a standard black enclosure.
Figure 3B:
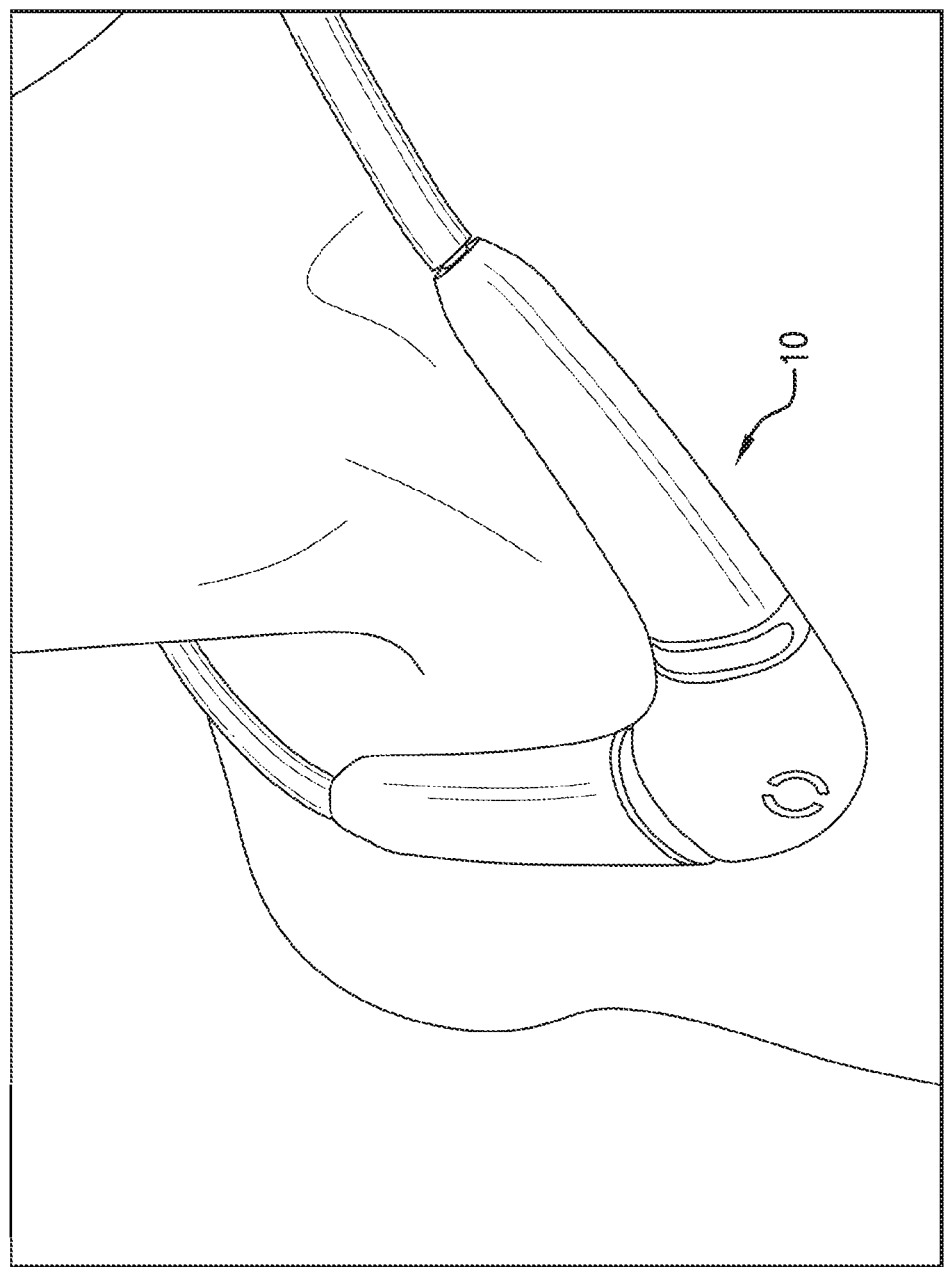
FIG. 3B is a photograph of an embodiment of a neck-worn sensor according to the invention, as illustrated in use in FIG. 2, with a decorative floral enclosure.

The rigid circuit boards 52a, 52b, and 54 are each encased inside of a rigid protective housing segments 53a, 53b, 55, and the flexible conductor segments 56a, 56b are encased within the flexible connector segments 46 and 48. The material of the protective housing segments 53a, 53b, and 55 is shown as clear or transparent in FIGS. 4, 6A-6C, 9, and 10 and 10A in order to better show the underlying circuit components. The protective housing segments 53a, 53b, and 55 are more typically made from opaque plastic, as illustrated in FIGS. 3A and 3B, which contributes to the overall aesthetically pleasing appearance of the sensor 10. In other embodiments, as shown particularly in FIG. 3B, the protective housing segments can be made from plastic coated with a decorative pattern, such as a floral pattern. Or in other embodiments, clip-on coverings or decals can be applied to the protective housing segments to occasionally change the appearance of the sensor, e.g. to make it match a particular article of clothing. This can also make the sensor appear like conventional jewelry, which in turn may make a patient more likely to wear it.

Suitably, the connector segments 46 and 48, which may be formed as rubber boots designed to snap into respectively opposing ends of the protective housing segments 52a, 52b, and 54, are typically made from soft, flexible material such as silicone rubber. Generally speaking, such a configuration of the sensing portion 30 serves to hold the sensing electrodes at their proper positions before they are adhered to the patient's chest, while allowing the sensing portion 30 to conform to the different curvatures of the physiological region upon which it rests.

Figure 4:
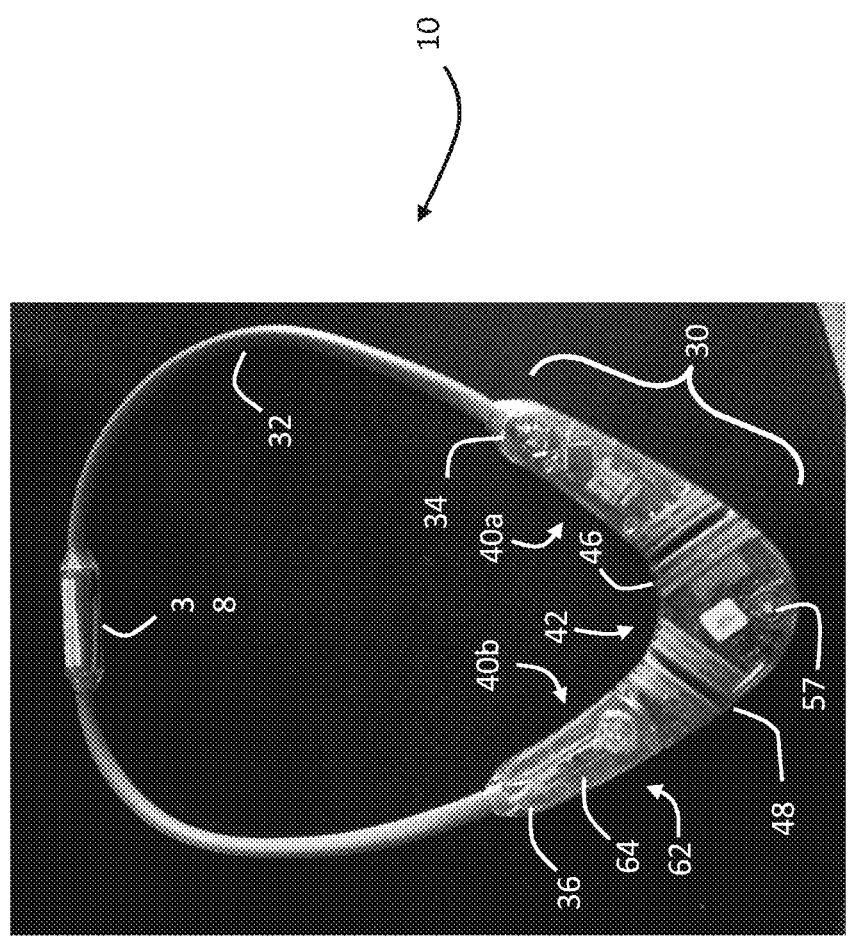
FIG. 4 is a photograph of an embodiment of a neck-worn sensor according to the invention as illustrated in use in FIG. 2, with a transparent housing to reveal its internal components.

As further illustrated in FIGS. 3 and 4, a transparent or translucent plastic window 57 located on the top, anteriorly facing surface of central housing segment 55 covers an underlying LED 59, which serves as a simple user interface for the patient 12. For example, the LED 59 can radiate different colors of the visible spectrum, and blink them at different frequencies, to indicate when the sensor 10 is turned on, making a measurement, charging, running on low power, completed with a measurement, etc.

As shown most clearly in FIGS. 5 and 6A-6C, a pair of conductors 58 (e.g., a twisted pair of braided-strand or solid-core wiring) supplies power and ground from the sensor's battery to circuitry housed within the segments 40a, 40b, and 42 of the sensing portion 30. The conductors 58 also supply a control ("enable") signal, described in more detail with respect to FIG. 8, that serves to power on the sensor. More specifically, the conductors 58 are electrically connected to and extend from electrical components on one of the rigid circuit boards (e.g., circuit board 52a). The conductors 58, which are sheathed in silicone or other soft material that will be comfortable when worn around the patient's neck, are also electrically connected at their distal ends to components on the clasp circuit board 64 of a magnetic-switch clasp assembly 62.

The magnetic-switch clasp assembly 62 houses the clasp circuit board 64 and a magnetic connector 68. Suitably, the silhouette or planform contours of the clasp assembly 62 match those on the upper surface of the protective housing segment 53b encasing the rigid circuit board. Furthermore, that protective housing segment has a slight recess 66 in its upper or anterior-facing surface and into which the clasp assembly 62 fits. The recess 66 allows the clasp assembly 62 to mate with the protective housing segment 53b in a way that forms a mostly smooth, generally continuous upper surface, as best shown in FIGS. 3A, 3B, and 6C.

Figure 5:
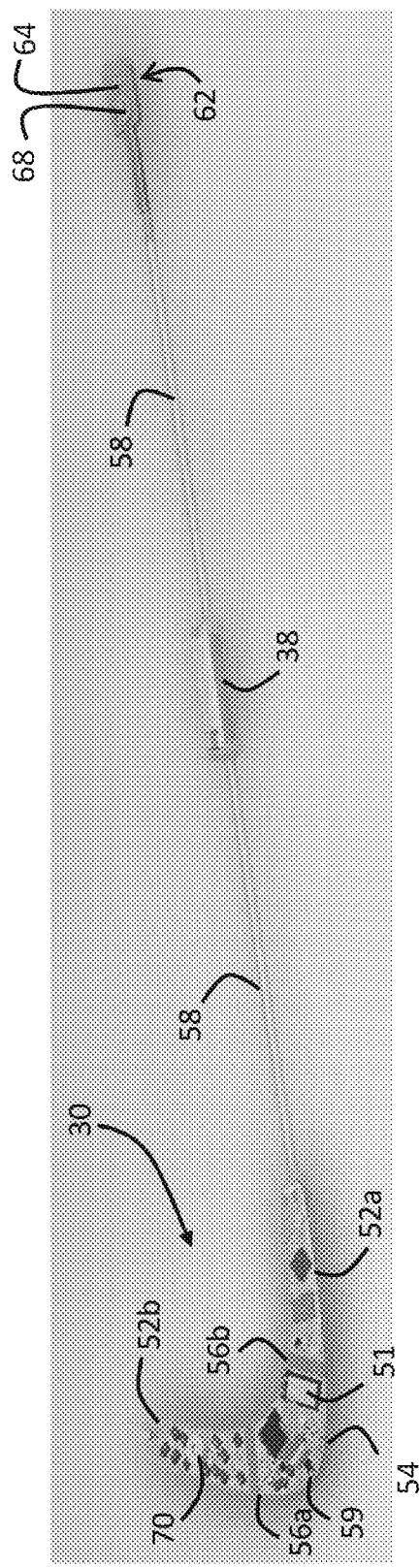
FIG. 5 is a perspective view of the neck-worn sensor shown in FIGS. 3 and 4, with its housing removed to show arrangement of its internal circuit boards and other electrical components.
Figure 6A:
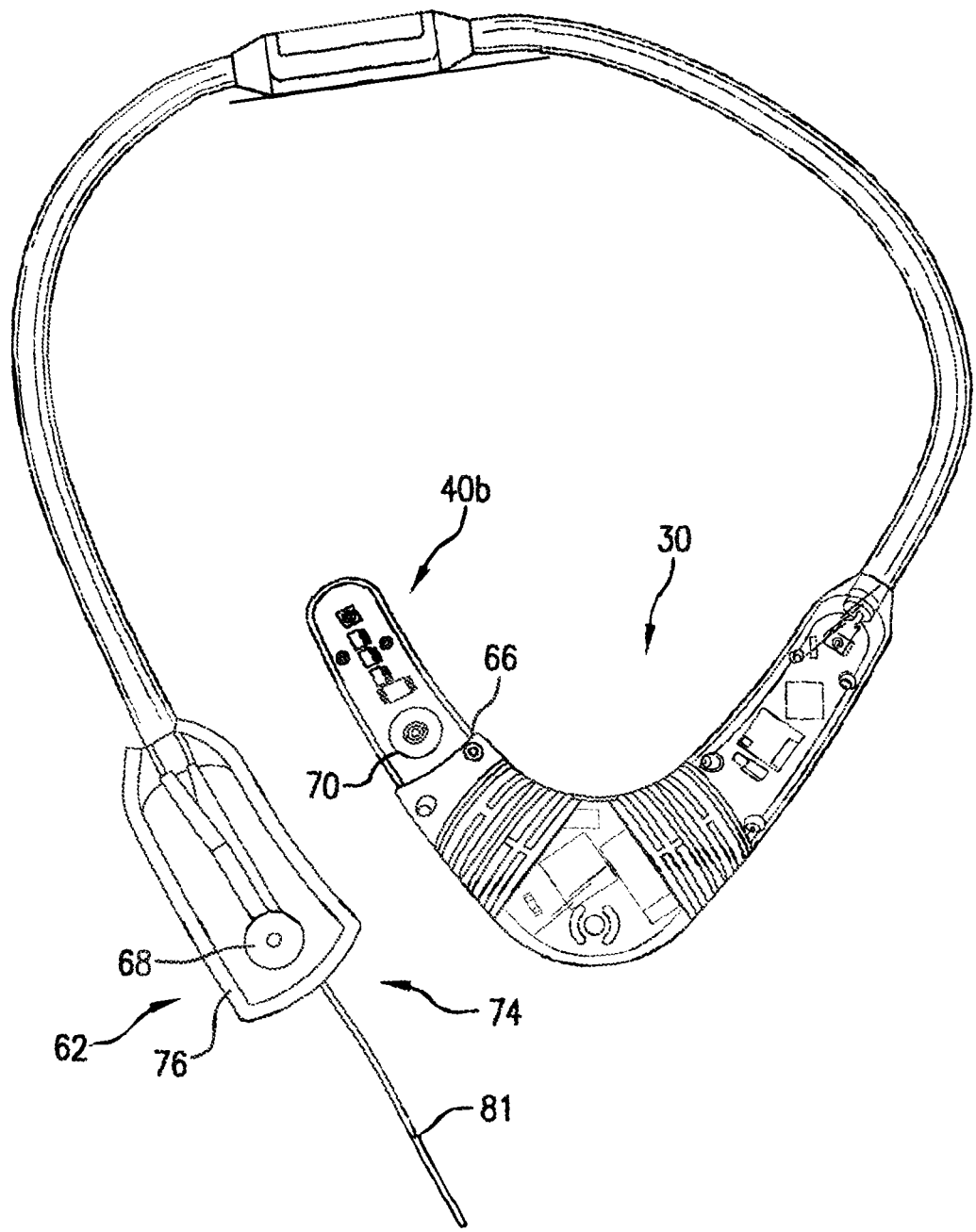
FIG. 6A is a photograph of the sensor shown in FIGS. 3 and 4, with its magnetic clasp portion attached to a battery charger.
Figure 6C:
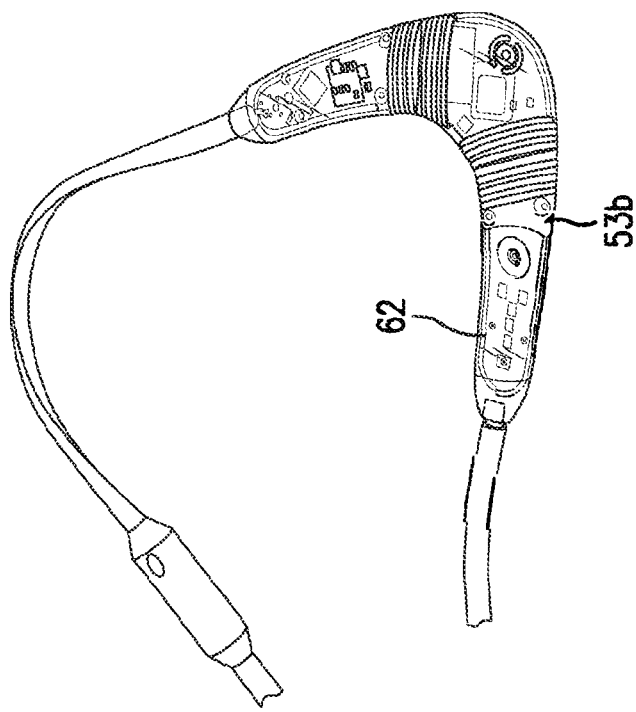
FIGS. 6B and 6C are photographs of the sensor shown in FIGS. 3 and 4, with, respectively, its magnetic clasp attached and detached from its base sensing portion.
Figure 6B:
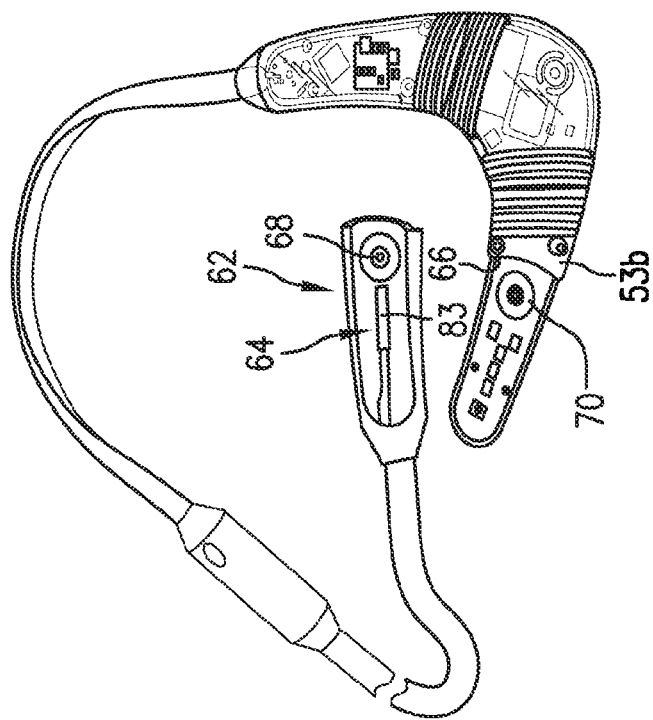

As further shown in FIGS. 5 and 6B-6C, a first clasp magnet 68 is attached to the clasp circuit board 64 within the clasp assembly 62 and is partially exposed. A second clasp magnet 70 is attached to the rigid circuit board 52b within the outboard sensor segment 40b and is partially exposed/accessible through the housing 53b. Suitably, the first and second clasp magnets 68, 70 are oppositely polarized rare-earth magnets that are coated with a film of conductive metal (e.g., chromium). They are electrically connected to circuitry located on the clasp circuit board 62 and the rigid circuit board 52b, respectively.

The first and second clasp magnets 68 and 70 are positioned on the clasp circuit board 64 and rigid circuit board 52b, respectively, so that when the clasp assembly 62 is mated with the protective housing segment 53b as shown, for example, in FIG. 6C, the magnets 68 and 70 are brought into engagement with each other. Furthermore, the first and second clasp magnets 68, 70 are oriented so that opposite polarities thereof will face each other when the clasp assembly 62 is mated with the protective housing segment 53b. As a result, the first and second clasp magnets 68 and 70 are able to releasably secure the magnetic-switch clasp assembly 62 to the outboard sensor segment 40b.

So engaging the magnetic-switch clasp assembly 62 to the sensor segment 40b—and, more particularly, connecting the clasp magnets 68 and 70 to each other—completes a circuit (described below in conjunction with FIG. 8) that functions as a control circuit within the clasp circuit board 64. This powers on the sensor 10 and drives the control circuit to supply power from the battery to the sensor portion 30, thereby causing the sensor 10 to turn on and initiate a measurement, as described in more detail below.

From this description of the conductors 58 and the magnetic-switch clasp assembly 62 located at the end of them, it will be appreciated that the pair of conductors 58 function as the securement member 32 by means of which the sensor 10 is worn around the patient's neck 28 in the illustrated embodiment. Furthermore, as shown most clearly in FIGS. 4, 5, and 6A and as alluded to above, the battery compartment 38 is located generally halfway along the length of the securement member 32/conductors 58. Suitably, the battery compartment can be formed as a cylindrical capsule into which a rechargeable lithium ion battery fits. (For the disclosed embodiment, the battery preferably generates 4.2V when it is fully charged and 3.3V when it is depleted.) Although not specifically illustrated, the capsule may be formed from two half-cylindrical portions—possibly joined along lengthwise-extending edges that form a hinge—that snap together to enclose the battery within the compartment 38. In other non-illustrated embodiments, the battery can be removable, and be replaced in the compartment. Electrical contacts (not illustrated) are located at opposite ends of the battery compartment 38 and engage the positive and negative terminals of the battery when the battery is inserted into the battery compartment 38. This configuration allows a completed circuit to be formed when the magnetic-switch clasp assembly 62 is engaged with the sensor segment 40b as described above.

Figure 7:
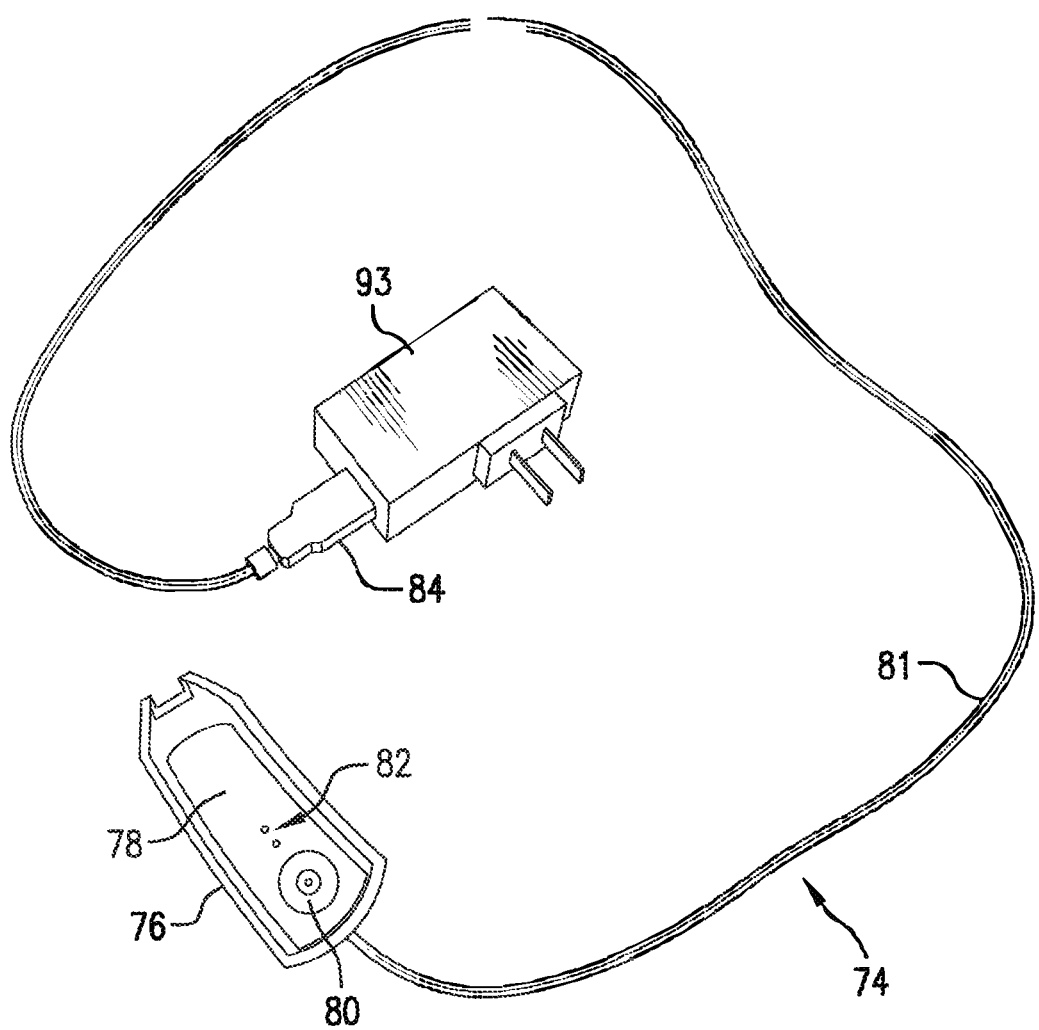
FIG. 7 is a photograph of the battery charger, configured to charge a battery housed within the sensor when mated with the magnetic clasp portion shown in FIGS. 6A, 6B, and 6C.
Figure 8:
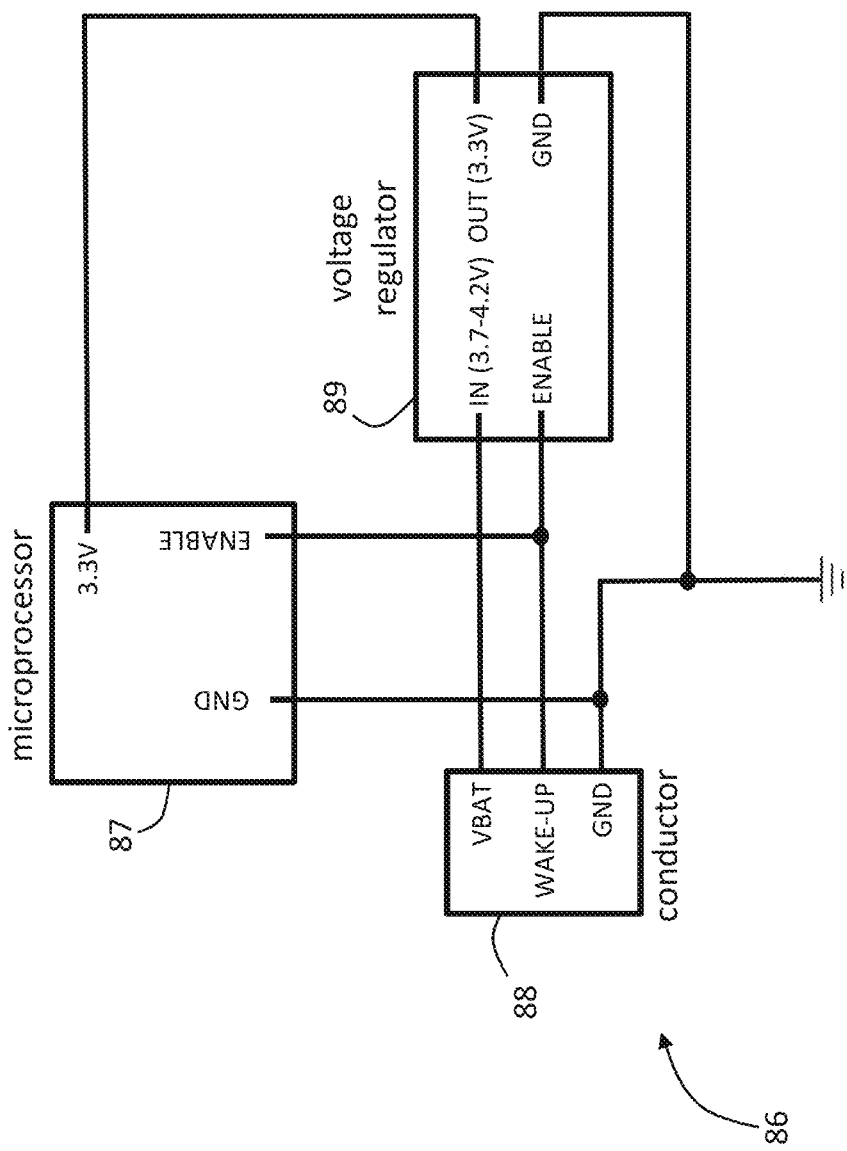
FIG. 8 is a schematic circuit diagram of a circuit that controls powering of the sensor and charging of its battery.

Advantageously with this configuration, a battery charger 74 as illustrated in FIGS. 6A, 7, and 8 can be provided with the sensor 10 to charge the sensor's lithium ion battery. The battery charger 74 has a plastic receptacle member 76 with a depression-shaped receptacle region 78 configured to engage with the exterior-facing surface of the clasp assembly 62. A charger magnet 80 is attached to or partially embedded within the receptacle region 78 and is positioned within the receptacle region so as to engage with the switch clasp magnet 68 when the clasp assembly 62 is brought into engagement with the receptacle member 76. Furthermore, the charger magnet 80 is oriented such that opposite polarities of the charger magnet 80 and the clasp magnet 68 will face each other then the clasp assembly 64 engages with the receptacle member 76. Like the clasp magnets 68, 70, the charger magnet 80 is a rare-earth magnet that is coated with a film of conductive metal (e.g., chromium).

A signal-conducting cable 81 passes partially through and out of receptacle member 76 and terminates in a standard USB plug 84, with one electrical conductor (not shown) that is contained within the cable 81 being electrically connected to the charger magnet 80. Furthermore, a pair of spring-loaded contact pins 82 (commonly called 'pogo pins') extend into the receptacle region 78, and are positioned to make contact with a corresponding pair of electrical contacts 83 that are located on the clasp circuit board 64 and that are accessible via a corresponding pair of holes formed in the clasp assembly 62, as shown in FIG. 6B. Two additional electrical conductors (not shown) that are contained within the cable 81 are electrically connected to the pins 82 and supply power (+5V) and ground to the electrical contacts 83 on the clasp circuit board 64 when the magnetic-switch clasp assembly is properly mated with the battery charger 74. The USB plug 84 can plug into the USB outlet of a personal computer or a common AC/DC converter 93 (with a female USB socket) that converts, e.g., 120V AC current from a standard outlet to +5V DC.

To charge the sensor's battery, the anterior-facing surface of the clasp assembly 62 is brought into engagement with the receptacle region 78, thus causing the clasp magnets 68 and 80 to engage each other and releasably and magnetically secure the clasp assembly 62 within the receptacle 78. This action causes a circuit to be completed and causes the control circuit in the clasp circuit board to power on the sensor, as explained immediately below. When this happens, DC power from the AC/DC converter 93 or USB outlet of a personal computer passes through the USB plug 84, along the conducting cable 81, through the pins 82, and to the electrical contacts 83 disposed on the clasp circuit board 64. This action fully charges the battery over a period of about 4 hours.

Operation and one possible arrangement of the control circuit 86 are illustrated in FIG. 8 (note that the circuit shown in the figure is a simplified version of the actual circuit schematic corresponding to the sensor). The circuit enables powering of the sensor using the clasp assembly 62, as well as charging of the battery with the battery charger 74. In both cases, voltage directly from the battery (typically between 3.7 and 4.2V) is connected directly to the WAKE UP line in the conductor 88. To power the sensor, the magnetic-switch clasp assembly 62 engages with the sensor segment 40*b*, causing clasp magnets 68 and 70 to connect to each other. This supplies voltage directly from the WAKE UP line to ENABLE pins in both the voltage regulator 89 and microprocessor 87, thus enabling these components to function as designed. Once this occurs, the voltage regulator 89 trims an input voltage from the battery to 3.3V, which leaves the voltage regulator from the OUT line to power the microprocessor 87 and most other digital components in the sensor. At this point, the microprocessor is enabled, and can carry out all necessary functions, such as switching on circuitry and blinking any LEDs, even if the clasp assembly 62 is disconnected. A similar situation exists with the battery charger 74 when the clasp assembly 62 is brought into engagement with the receptacle region 78, thus causing the magnets 68 and 80 to contact each other. When this occurs, the microprocessor is powered and enabled as described above, and in response shuts down all power-consuming analog circuitry in the sensor. This allows the battery to charge in an efficient manner when it is placed in the battery charger 74, as described above.

Figure 9A:
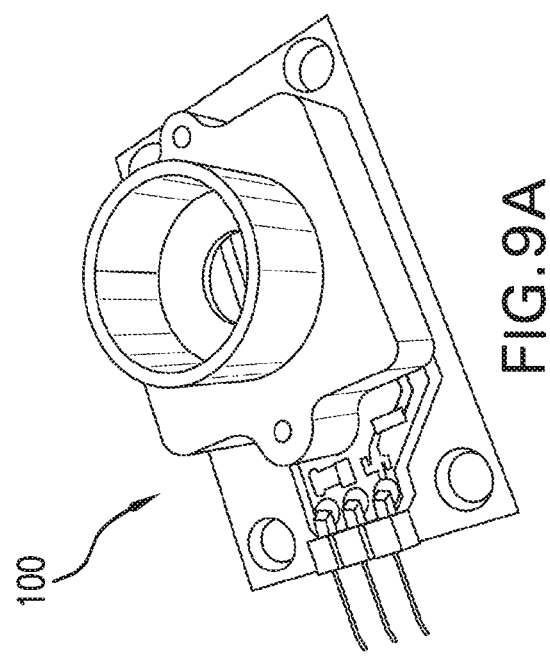
FIG. 9A is a perspective view of pulse oximetry circuitry included in the circled portion of FIG. 9.
Figure 9:
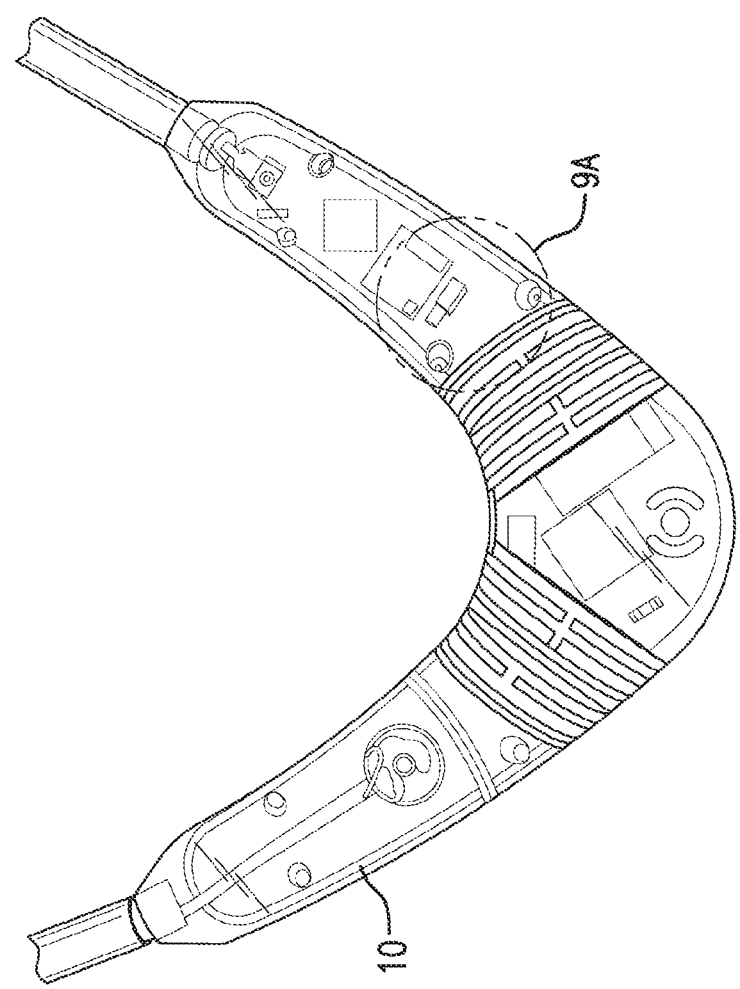
FIG. 9 is a photograph of the sensor in use, with a transparent housing to reveal internal components thereof, and which front view is provided for reference for FIG. 9A.

As shown in FIGS. 9 and 9A, the sensor 10 can also include a standard pulse oximetry circuit 100 such as the one described in U.S. Pat. No. 8,437,824, the contents of which are incorporated by reference in their entirety. Using a non-invasive, optical measurement, the pulse oximetry circuit 100 generates a value of SpO2. It may be located on the rear, patient-facing side of one of the sensor's outboard circuit boards, e.g., on circuit board 52*a*, and generally near the attachment points for a pair of electrodes that are used with the sensor (as explained in greater detail below). The pulse oximetry circuit 100 drives red and infrared LEDs in an alternating, pulsatile manner and controls a light-sensitive, photodetector diode, as generally known in the art. (FIG. 9A illustrates an integrated module, in which the LEDs and photodetector are not independently discernible; because this technology is well known in the field, they are not identified individually in the figures.)

The pulse oximetry circuit 100 is configured to operate in a reflection mode, meaning that the LEDs and light-sensitive diode are positioned so as to receive radiation from the same direction. It measures PPG waveforms from capillary beds in the patient's chest to generate a value of SpO2, as is described in more detail below. This is in contrast to conventional pulse oximetry sensors in which the LEDs and the light-sensitive diode are positioned across from each other, with a space into which fits a body part (e.g., a finger or an earlobe) being located between the LEDs and the light-sensitive diode. Thus, the pulse oximetry circuit detects and measures radiation emitted by the diodes that has been reflected off of capillary beds (i.e., in the chest) before arriving at the light-sensitive diode.

Because the pulse oximetry sensor is incorporated into the overall sensor 10, the pulse oximetry optical sensor can connect comfortably to the patient's chest to measure SpO2 values in an effective manner that eliminates "cable clutter" and frees the patient's hands and fingers (where pulse oximetry measurements typically are taken) for other purposes. An additional benefit of this configuration is reduction of motion artifacts, which can distort PPG waveforms and cause erroneous values of SpO2 to be reported. This reduction of motion artifacts is due to the fact that during everyday activities, the chest typically moves less than the hands and fingers, and subsequent artifact reduction ultimately improves the accuracy of SpO2 values measured from the patient.

Finally with regard to the basic construction of a sensor 10 according to the invention, both a three-axis digital accelerometer and a temperature sensor (not specifically identified) are provided on the central circuit board 54 to measure, respectively, three time-dependent motion waveforms (along x, y, and z-axes) and TEMP values.

Bioelectric Signal-Acquiring and Signal-Processing Components

As noted above, a sensor 10 according to the invention monitors a patient by means of bioelectrical signals. In particular, electrical circuitry on the rigid circuit boards 52*a*, 52*b*, and 54 as well as the flexible circuits 56—working in conjunction with disposable electrodes that are attached to the outboard rigid circuit boards 52*a* and 52*b* as described more fully below—are designed to measure impedance and, from that impedance, yield the TBI waveform. The ECG waveform is measured in a known manner, and other relevant parameters can then be calculated from the TBI waveform as addressed below.

Figure 10:
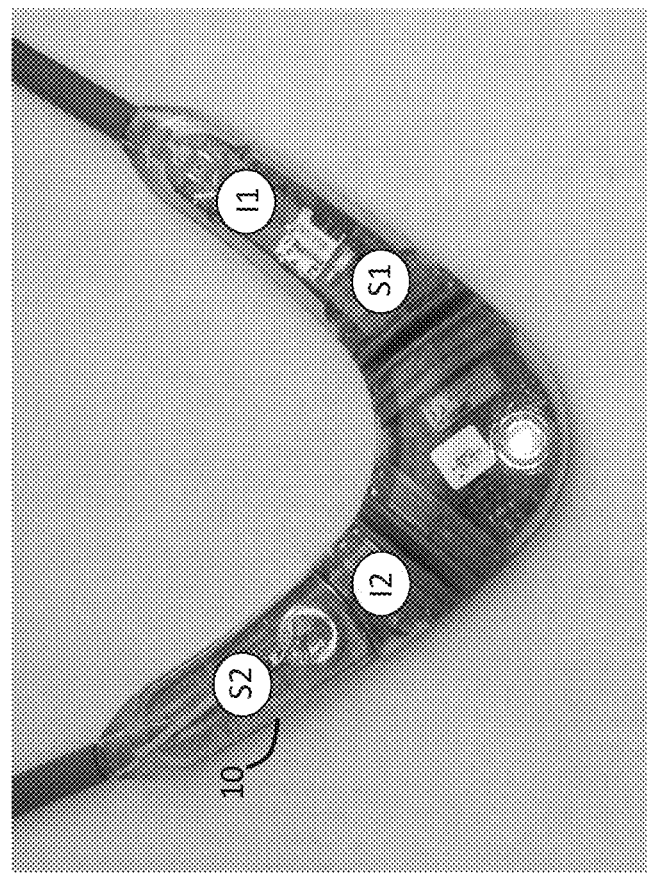
FIG. 10 is a photograph of the sensor in use, with a transparent housing to reveal internal components thereof and which front view is provided for reference for FIG. 10A.
Figure 10A:
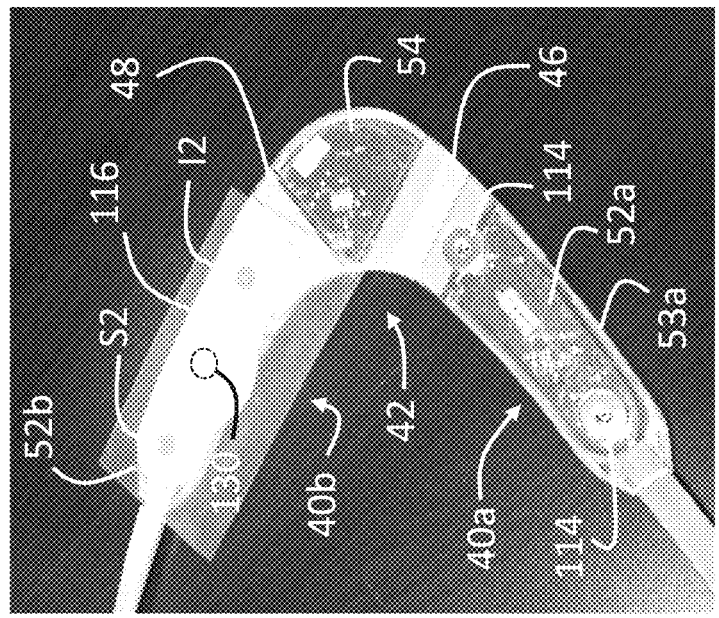
FIG. 10A is a photograph of the sensor's backside showing the use of magnetically attached electrode patches.

Thus, as shown in FIGS. 10 and 10A, each of the outboard rigid circuit boards 52*a* and 52*b* has a pair of circular, electrode-retaining rare-earth magnets 114 attached to it. (A two-part electrode patch 116 that magnetically connects to them hides the electrode-retaining magnets on circuit board 52*b*). The electrode-retaining magnets 114 are positioned within similarly sized circular openings in the rear walls of the protective housing segments 53*a* and 53*b*, and thus they are accessible from the rear exterior of the outboard segments 40*a* and 40*b*. Furthermore, each of the electrode-retaining magnets 114 has a conductive metal coating (e.g. chromium) and is electrically connected to the circuitry located on its respective circuit board 52*a* or 52*b*. As a result, the magnets 114 are able to conduct electrical signals sensed by the electrodes into the TBI and ECG analog circuits of the sensor 10.

Two-part electrode patches 116, which are suitable for use with a sensor 10 according to the invention, are generally known in the art. Construction of similar electrode patches is described, for example, in currently U.S. Patent Application No. 61/747,864, filed Dec. 31, 2013 (entitled "Body-worn Sensor for Characterizing Patients with Heart Failure"), the contents of which are incorporated herein by reference. In general, in such an electrode patch 116, an adhesive backing supports each of two distinct and electrically uncoupled conductive electrodes, and each of the electrodes has a sticky, conductive hydrogel that contacts the patient's skin. As shown in FIG. 10A, a small hole or aperture 130 on the order of 5 millimeters in diameter is formed through the electrode patch 116 to permit radiation associated with the pulse oximetry circuit 100 and the pulse oximetry measurement to pass through the electrode patch so that SpO2 values can be measured from capillary beds in the patient's chest. For each electrode, the hydrogel contacts an eyelet, which is coated on one side with a thin layer of Ag/AgCl, and is connected on its other side to a metal post made from conductive stainless steel.

Because the stainless steel metal posts of the electrode patches 116 are attracted to the magnets 114, electrode patches 116 can be attached to the sensor 10 relatively simply by holding an electrode patch near, and generally aligned with, one of the outboard sensor segments 40a or 40b, with the electrodes near the magnets 114. Magnetic attraction between the magnets 114 and the stainless steel posts will then cause the electrode patch 116 to snap into place (but removably so), thereby eliminating the need for cumbersome snaps and rivets that can be difficult for elderly patients to manipulate. Moreover, forces associated with pressing the electrodes' metal posts into the corresponding electrode holders of known, prior art-devices can cause circuit components to pop off, thus impeding performance of the device. Both these conditions are ameliorated to some extent by using magnets.

Thus, with a sensor 10 constructed as per the invention, electrode patches are connected to the sensing portion 30 first, and then they are connected to the patient by pressing the sensing portion 30, and hence the electrodes, against the patient's skin. Because the shape of the sensing portion 30 is essentially fixed (allowing for slight deviation as the sensing portion flexes at the flexible connector segments 46 and 48), applying the electrodes to the patient's skin in this manner facilities relatively consistent and accurate location of the electrodes on the patient, thereby enhancing the accuracy—especially over time—and hence the value of the information obtained with the sensor 10. Additionally, proper location and spacing of the electrodes ensures both TBI and ECG waveforms are acquired with high signal-to-noise ratios; this, in turn, leads to measurements that are relatively easy to analyze and that, as a result, have optimized accuracy.

The circuit boards 52a, 52b, and 54 have arranged thereon a first electrical circuit for making an impedance-based measurement of TBI waveforms that yield CO, SV, RR, and fluid levels, and a second electrical circuit for making differential voltage measurements of ECG waveforms that yield HR and arrhythmia information. The first electrical circuit 134 is illustrated schematically in FIG. 14; understanding of the arrangement and functionality of the components that comprise the first electrical circuit 134 will, however, be facilitated by a preceding explanation of the bioelectrical signal-acquisition and processing functions performed by the circuitry. Furthermore, the second electrical circuit is of a type that is well known in this particular art, and thus it is not described in significant detail herein.

As indicated schematically in FIGS. 10 and 10A, each electrode patch 116 includes a current-injecting electrode region I1, I2 described in detail below. (It should be noted that just a single electrode patch 116 is shown in FIG. 10A but that during use of a sensor 10 according to the invention, an electrode patch 116 is attached to the electrode-retaining magnets 114 on both lateral sides of the sensor 10.) Each electrode patch 116 also includes another, voltage-sensing electrode regions S1, S2. During a measurement, the S1, S2 regions sense bioelectric signals. These pass through a first circuit, which includes a collection of filters, amplifiers, and rectifying components that generate a time-dependent, analog TBI waveform that relates by Ohm's Law to impedance encountered by the injected current. This is explained in detail below with respect to FIG. 13. Likewise, the bioelectric signals also pass through a second circuit, which features a differential amplifier and filtering components that generate a time-dependent, analog ECG waveform. Such a circuit is standard in this particular art, and is thus not described in detail here.

Thus, to use the sensor 10 to monitor a patient's physiology, an electrode patch 116 is first attached to the sensing portion 30 of the sensor 10, and then the electrodes are attached to the patient's chest as noted above. Ideally, each electrode patch 116 attaches just below the patient's collarbone, near the patient's left and right arms. During a measurement, the impedance circuit (described more fully below) injects a high-frequency, low-amperage current (I) into the patient's skin through electrode regions I1, I2. Typically, the modulation frequency is about 70 kHz, and the current is about 6 mA. The current injected by each electrode region I1, I2 is out of phase by 180° with respect to the other. It encounters static (i.e. time-independent) resistance from components such as fluids and, to a lesser extent, bone, skin, and other tissue in the patient's chest. Additionally, blood and other fluids in the chest conduct the current to some extent. Blood ejected from the left ventricle of the heart into the aorta provides a dynamic (i.e. time-dependent) resistance. As the largest artery passing blood out of the heart, the aorta has a dominant impact on the dynamic resistance; other vessels such as the superior vena cava, on the other hand, will contribute to the dynamic resistance in a minimal way.

Electrode regions S1, S2 measure a time-dependent voltage (V) that varies with resistance (R) encountered by the injected current (I) according to Ohm's Law, shown below in Equation 3:

$$V = I \times R \tag{3}$$

During a measurement, the time-dependent voltage is filtered by the impedance circuit and ultimately measured with an analog-to-digital converter within the electronic circuitry. This digitized voltage is then processed to calculate SV using an equation such as that shown below in Equation 4, which is the Sramek-Bernstein equation, or a mathematical variation thereof. Historically, parameters extracted from TBI signals are fed into the equation, shown below, which is based on a volumetric expansion model taken from the aortic artery:

$$SV = \delta \frac{L^3}{4.25} \frac{(dZ(t)/dt)_{max}}{Z_0} LVET \tag{4}$$

In Equation 4, Z(t) represents the TBI waveform, δ represents compensation for body mass index, $Z_0$ is the base impedance, L is estimated from the distance separating the current-injecting and voltage-measuring electrodes on the thoracic cavity, and LVET is the left ventricular ejection time, which is the time separating the opening and closing of the aortic valve. An averaged value of $Z_0$ is equivalent to TFI and will vary with fluid levels. Typically, a high resistance (e.g. one above about 30Ω) indicates a dry, dehydrated state. In that case, the lack of conducting thoracic fluids increases resistivity in the patient's chest. Conversely, a low resistance (e.g. one below about 19Ω) indicates the patient has more thoracic fluids, and is possibly overhydrated. In that case, the abundance of conducting thoracic fluids decreases resistivity in the patient's chest. LVET can be determined from the TBI waveform, or from the HR using an equation called "Weissler's Regression," shown below in Equation 5, that estimates LVET from HR:

$$LVET = -0.0017 \times HR + 0.413 \qquad (5)$$

Weissler's Regression allows LVET to be estimated from HR determined from the ECG waveform. This equation and several mathematical derivatives, along with the parameters shown in Equation 4, are described in detail in the following reference, the contents of which are incorporated herein by reference: *"Impedance Cardiography, Pulsatile blood flow and the biophysical and electrodynamic basis for the stroke volume equations,'* Bernstein, *Journal of Electrical Bioimpedance*, Vol. 1, p. 2-17, 2010. Both the Sramek-Bernstein Equation and an earlier derivative of this, called the Kubicek Equation, feature a "static component," $Z_0$, and a "dynamic component," $Z(t)$, the derivative of which relates to LVET and a $(dZ/dt)_{max}/Z_0$ value. These equations assume that $(dZ(t)/dt)_{max}/Z_0$ represents a radial velocity of blood (with units of Ω/s) due to volume expansion of the aorta.

Figure 13:
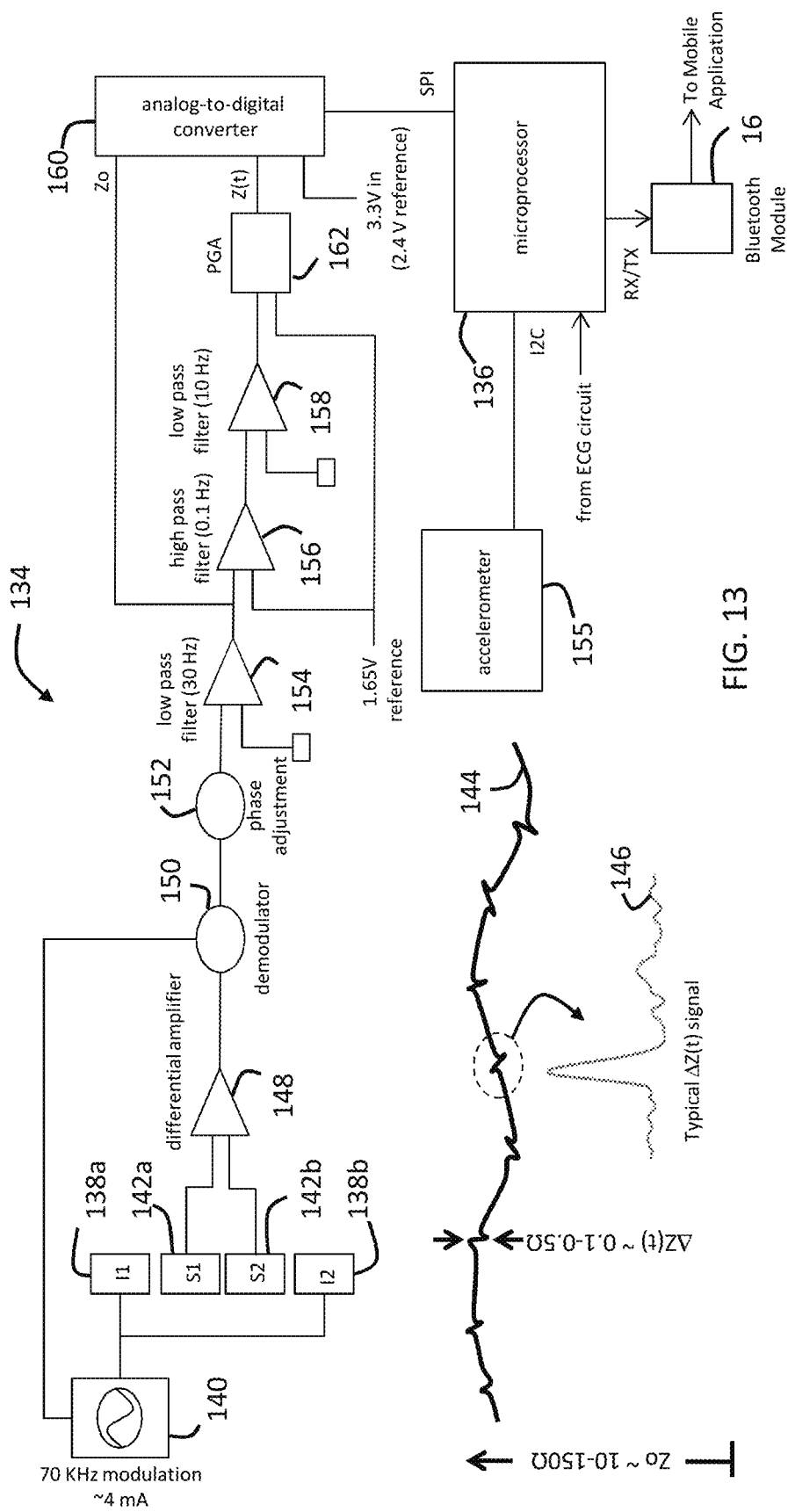
FIG. 13 is a schematic diagram of a circuit within the sensor used to measure TBI waveforms.

Furthermore, during a measurement, the second electrical circuit measures an analog ECG waveform that is received by an internal analog-to-digital converter within the onboard microprocessor 136 (shown in FIG. 13). An algorithm processes the waveform to determine HR and SYS/DIA, as described in more detail below. Additionally, the microprocessor 136 analyzes this signal simply to determine whether the electrode patches are properly adhered to the patient and that the system is operating satisfactorily. An ECG waveform of high quality (e.g. having a signal-to-noise ratio>5) indicates that electrode patches are properly adhered, while one of low quality (e.g. having a signal-to-noise ratio<5) indicates the opposite. Once this state is achieved, the first and second electrical circuits generate time-dependent analog waveforms that a high-resolution analog-to-digital converter within the electronics module receives and sequentially digitizes to generate time-dependent digital waveforms. Typically, these waveforms are digitized with 16-bit resolution over a range of about 10V. The microprocessor receives the digital waveforms and processes them with computational algorithms, written in embedded computer code such as C or Java, to generate values of CO, SV, TFI, and HR, as is described in more detail below Further still, during a measurement, the light-sensitive diode in the pulse oximetry circuit 100 receives radiation from the associated LEDs that reflects off of tissue. Signals from the light-sensitive diode pass through amplifier and filter circuitry to yield PPG waveforms emanating from the red and infrared radiation. These waveforms are digitized with an analog-to-digital converter and then processed to extract fiducial points, as described in the above-referenced-and-incorporated '824 patent. The fiducial points are then processed with an algorithm that implements Equation 6, below, to determine a SpO2 value.

$$R = \frac{red(AC)/red(DC)}{infrared(AC)/infrared(DC)} \qquad (6)$$

In Equation 6, the red (AC) and red (DC) represent, respectively, parameters extracted from the AC and DC components of the PPG waveform measured with the red LED. A similar case holds for the infrared (AC) and infrared (DC) values. The term "AC signals", as used herein, refers to a portion of a PPG waveform that varies relatively rapidly with time, e.g., the portion of the signal caused by pulsations in the patient's blood. "DC signals," in contrast, are portions of the PPG that are relatively invariant with time, e.g., the portion of the signal originating from scattering off of components such as bone, skin, and non-pulsating components of the patient's blood.

More specifically, AC signals are measured from a heartbeat-induced pulse present in both waveforms. The pulse represents a pressure wave, launched by the heart, which propagates through the patient's vasculature and which causes a time-dependent increase in volume in both arteries and capillaries. When the pressure pulse reaches vasculature irradiated by the oximeter's optical system, a temporary volumetric increase results in a relatively large optical absorption according to the Beer-Lambert Law. DC signals originate from radiation scattering from static components such as bone, skin, and relatively non-pulsatile components of both arterial and venous blood. Typically, only about 0.5% to about 1% of the total signal measured by the pulse oximetry photodetector is attributable to the AC signal, with the remainder being attributable to the DC signal. Separation of AC and DC signals is typically done with both analog and digital filtering techniques that are well-known in the art.

The R value in Equation 6, which is sometimes called a "ratio of ratios" (RoR), represents a ratio of hemoglobin Hb to oxygenated hemoglobin HbO2. It equates an actual SpO2 value, which ranges from 0-100% O2, to an empirical relationship that resembles a non-linear equation. Above about 70% O2, this equation typically yields values that are accurate to within a few percentage points. On the other hand, while not necessarily accurate, measurements below this value still indicate a hypoxic patient in need of medical attention. Additional details for this calculation are described in the above-referenced-and-incorporated patent.

As noted above, the pulse oximetry circuit 100 operates in a reflection mode. Therefore, radiation from the pulse oximetry diodes passes through the hole 130 in the electrode patch to tissue in the chest and then reflects back before arriving at the pulse oximetry light-sensitive diode, where this component and the pulse oximetry circuit process it to form the requisite PPG waveforms needed for Equation 6. A conventional PPG waveform measured with the above-described optical sensor features a sequence of heartbeat-induced pulses, with the time duration separating the pulses being inversely related to PR. The heartbeat-induced pulses represent blood pulsing in an underlying artery that absorbs (or reflects) incident radiation from the red and infrared LEDs. The PPG waveform also includes a slowly varying baseline that is due to underlying optical absorption by the blood. PPG waveforms emanating from both waveforms look similar, with that from infrared radiation typically having a relatively high signal-to-noise ratio.

Figure 11A:
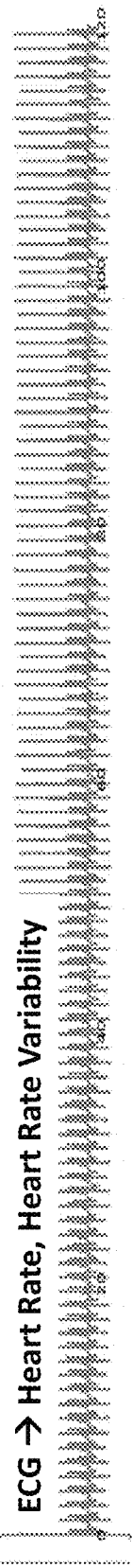
FIGS. 11A-11E are, respectively, graphs illustrating the following time-dependent waveforms.
Figure 11B:

FIGS. 11A-11E show ECG and TBI waveforms measured using the sensor 10. Waveforms shown in the figures are digital waveforms, sampled at a rate of 250 Hz. A typical ECG waveform (FIG. 11A) features a collection of "QRS complexes," with each QRS complex representing an individual heartbeat; the waveform shown in FIG. 11A is similar to a standard ECG waveform measured by a conventional vital sign monitor. FIGS. 11B-11E show different versions of the TBI waveform generated using analog and digital filtering processes that are implemented by the sensor 10. Analog filtering is typically performed with a standard RC circuit located directly on the sensor's circuit boards, whereas digital filtering is typically performed using software algorithms operating on the sensor's onboard microprocessor (shown in FIG. 13, which is described below).

Figure 11C:
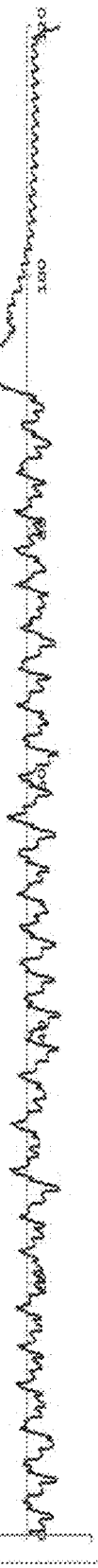
Figure 11D:
Figure 11E:

In general, analog and digital filtering techniques are well known in the art. As applied in the context of the present invention, they can be used to isolate AC (i.e., rapidly varying) and DC (i.e., slowly varying) components of the waveforms, which, in turn, yield different physiological parameters. For example, the DC component of the TBI waveform is sensitive to thoracic fluid levels and thus yields TFI. In particular, as thoracic fluid levels increase, the DC impedance measured by the sensor 10, shown as a relatively flat line in FIG. 11B, will decrease. The unprocessed AC component of the TBI waveform, shown in FIG. 11C, shows oscillating, time-dependent features corresponding to different physiological events (e.g. HR, RR) and that typically are isolated with digital filtering. As shown in FIG. 11D, processing the AC component of the TBI waveform with a low-pass (LP) filter removes relatively high-frequency components, thus yielding a relatively low-frequency undulation attributable to RR. This waveform can be further processed to identify periods of apnea, which are indicated by the lack of undulations in the waveform after about 100 seconds. Similarly, processing the AC component of the TBI waveform with a band-pass (BP) filter, as illustrated in FIG. 11E, selectively removes any low-frequency undulations. This leaves periodic, heartbeat-induced pulses attributable to blood flowing from the left ventricle into the aorta. These pulses can be processed to yield both SV and CO, as described further below.

Figure 12A:
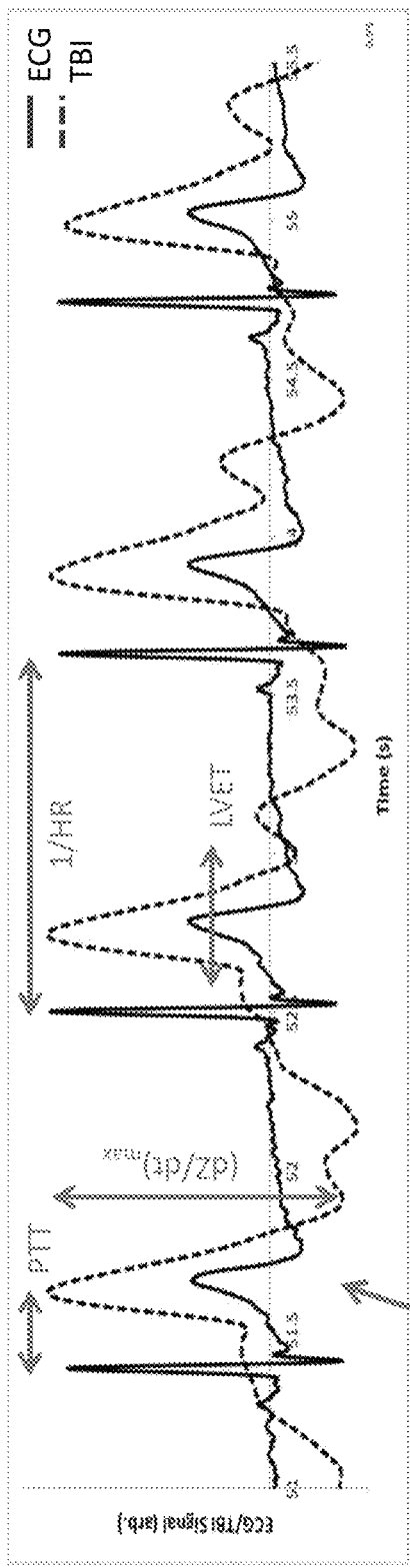
FIGS. 12A and 12B are, respectively, graphs illustrating the following time-dependent waveforms.
Figure 12B:
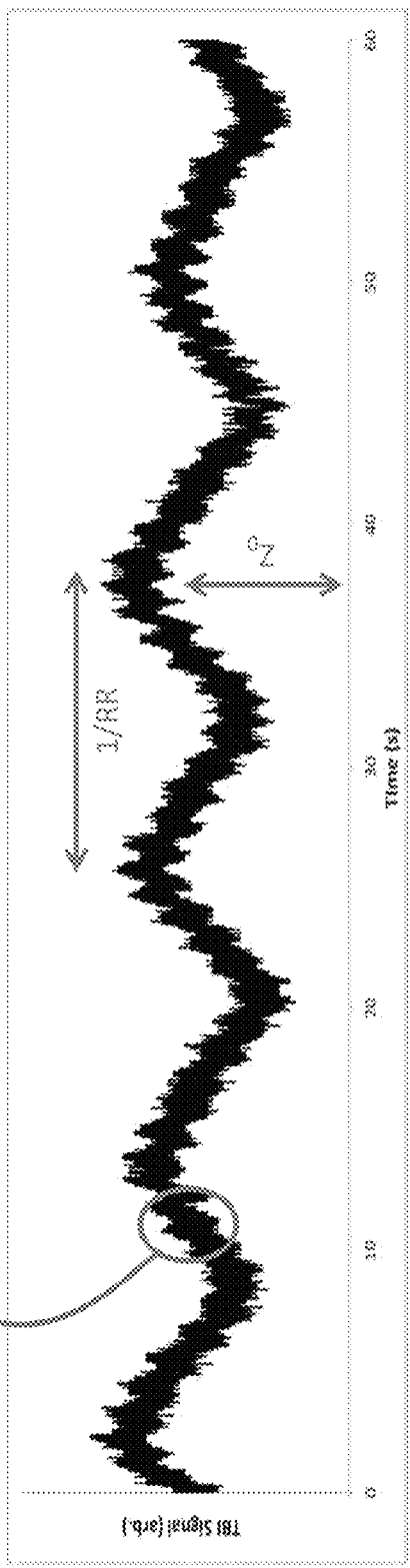

FIGS. 12A and 12B, in turn, show derivatized TBI and ECG waveforms measured with the sensor 10, as plotted over a short time window (i.e., about 5 seconds) in FIG. 12A and a longer time window (i.e., about 60 seconds) in FIG. 12B. As shown more clearly in FIG. 12A, individual heartbeats produce time-dependent pulses in both the ECG and TBI waveforms. As is clear from the data, pulses in the ECG waveform precede those in the TBI waveform. The ECG pulses, which each feature a sharp, rapidly rising QRS complex, indicate initial electrical activity in contractions in the patient's heart and, informally, the beginning of the cardiac cycle. The QRS complex is the peak of the ECG waveform. TBI pulses follow the QRS complex by about 100 ms and indicate blood flow through arteries in the patient's thoracic cavity. These signals are dominated by contributions from the aorta, which is the largest artery in this region of the body. During a heartbeat, blood flows from the patient's left ventricle into the aorta, and the volume of blood is the SV. Blood flow enlarges this vessel, which is typically very flexible, and also temporarily aligns blood cells from their normally random orientation. Both of these mechanisms—enlargement of the aorta and temporary alignment of the blood cells—improve electrical conduction near the aorta, thus decreasing the electrical impedance as measured with TBI. The TBI waveform shown in FIG. 12A is the first mathematical derivative of the raw TBI waveform; therefore, its peak represents the point of maximum impedance change.

A variety of time-dependent parameters can be extracted from the ECG and TBI waveforms. For example, as indicated in the upper portion of the figure, it is well known that HR can be determined from the time separating neighboring ECG QRS complexes. Likewise, LVET can be measured directly from the TBI pulse. LVET is measured from the onset of the derivatized pulse to the first positive-going zero crossing. Also measured from the derivatized TBI pulse is $(dZ/dt)_{max}$, which is a parameter that is used to calculate SV as shown in Equation 4 above and as described in more detail in the above-cited-and-incorporated literature reference.

The time difference between the ECG QRS complex and the peak of the derivatized TBI waveform represents a PTT. This value can be calculated from other fiducial points, particularly on the TBI waveform (such as the base or midway point of the heartbeat-induced pulse). Typically, however, the peak of the derivatized waveform is used, as it is relatively easy to develop a software beat-picking algorithm that finds this fiducial point.

In other, non-illustrated embodiments, the sensor can calculate VTT from fiducial points (e.g. the base or maximum value of the derivatized waveform) of each pulsatile component contained in both the PPG and TBI waveforms. VTT can then be used in place of PTT to calculate SYS. As described above, this approach has certain advantages, namely in that VTT lacks certain systolic time intervals (e.g. PEP, ICT) that do not depend on blood pressure, and may thus add errors to the blood pressure measurement. In other words, SYS calculated from VTT may be more accurate than SYS calculated from PTT.

PTT (and VTT) correlates inversely to SYS and DIA, as shown below in Equations 7 and 8, where $m_{SYS}$ and $m_{DIA}$ are patient-specific slopes for, respectively, SYS and DIA, and $SYS_{cal}$ and $DIA_{cal}$ are values, respectively, of SYS and DIA measured during a calibration measurement. (Without calibration, PTT only indicates relative changes in SYS and DIA.) A calibration can be provided with conventional means such as an oscillometric blood pressure cuff or in-dwelling arterial line. The calibration yields both the patient's immediate values of SYS and DIA. Multiple values of PTT and blood pressure can be collected and analyzed to determine patient-specific slopes $m_{SYS}$ and $m_{DIA}$, which relate changes in PTT with changes in SYS and DIA. The patient-specific slopes can also be determined by using pre-determined values from a clinical study and then combining these measurements with biometric parameters (e.g. age, gender, height, weight) collected during the clinical study.

$$SBP = \frac{m_{SBP}}{PTT} + SBP_{cal} \qquad (7)$$

$$DBP = \frac{m_{DBP}}{PTT} + DBP_{cal} \qquad (8)$$

In embodiments of a sensor 10 according to the invention, waveforms like those shown in FIG. 12A are processed to determine PTT, which is then used to determine either SYS or DIA according to Equations 7 and 8. Typically, PTT and SYS correlate to each other better than PTT and DIA, and thus this parameter is first determined. Then, PP is estimated from SV, calculation of which is described below. Most preferably, instant values of PP and SV are determined, respectively, from the blood pressure calibration and from the TBI waveform.

PP can be estimated from either the absolute value of SV, SV modified by another property (e.g. LVET), or the change in SV. In the first method, a simple linear model is used to process SV (or, alternatively, SV×LVET) and convert it into PP. The model uses the instant values of PP and SV, determined as described above from a calibration measurement, along with a slope that relates PP and SV (or SV×LVET). The slope can be estimated from a universal model that, in turn, is determined using a population study. Alternatively, a slope tailored to the individual patient is used. Such a slope can be selected, for example, using biometric parameters describing the patient, as described above. Here, PP/SV slopes corresponding to such biometric parameters are determined from a large population study and then stored in computer memory on the sensor 10. When a particular sensor unit is assigned to a patient, their particular biometric data is entered into the system, e.g. using a mobile telephone that transmits the data to the microprocessor in the sensor via Bluetooth® protocols. Then, an algorithm on the sensor processes the data and selects a patient-specific slope. Calculation of PP from SV is described in the following reference, the contents of which are incorporated herein by reference: "*Pressure-Flow Studies in Man. An Evaluation of the Duration of the Phases of Systole,*" Harley et al., *Journal of Clinical Investigation*, Vol. 48, p. 895-905, 1969. As explained in this reference, the relationship between PP and SV for a given patient typically has a correlation coefficient (r) that is greater than 0.9, which indicates excellent agreement between these two properties. Similarly, in the above-mentioned reference, SV is shown to correlate with the product of PP and LVET, with most patients showing an r value of greater than 0.93 and the pooled correlation value (i.e. that for all subjects) being 0.77. This last result indicates that a single linear relationship between PP, SV, and LVET may hold for all patients.

More preferably, PP is determined from SV using relative changes in these values. Typically, the relationship between the change in SV and change in PP is relatively constant across all subjects. Thus, similar to the case for PP, SV, and LVET, a single, linear relationship can be used to relate changes in SV and changes in PP. Such a relationship is described in the following reference, the contents of which are incorporated herein by reference: "*Pulse pressure variation and stroke volume variation during increased intra-abdominal pressure: an experimental study,*" Didier et al., *Critical Care*, Vol. 15:R33, p. 1-9, 2011. Here, the relationship between PP variation and SV variation for 67 subjects displayed a linear correlation of r=0.93, i.e., an extremely high value for pooled results that indicates a single, linear relationship may hold for all patients.

From such a relationship, PP is determined from the TBI-based SV measurement, and SYS is determined from PTT. DIA is then calculated from SYS and PP.

The sensor 10 determines RR from both the TBI waveform and a motion waveform generated by the accelerometer (called the ACC waveform). FIG. 12B illustrates how the TBI waveform yields RR. In this case, the patient's respiratory effort moves air in and out of the lungs, thus changing the capacitance (and hence impedance) in the thoracic cavity. This time-dependent change maps onto the TBI waveform, typically in the form of oscillations or pulses that occur at a much lower frequency than the heartbeat-induced cardiac pulses shown in FIG. 12A. Thus, simple signal-processing (e.g. filtering, beat-picking) of the low-frequency, breathing-induced pulses in the waveform yields RR.

Similarly, the ACC waveform will reflect breathing-induced movements in the patient's chest. This results in pulses within the waveform that have a similar morphology to those shown in FIG. 12B for the TBI waveform. Such pulses can be processed as described above to estimate RR. RR determined from the ACC waveform can be used by itself, or it can be processed collectively with RR as determined from the TBI waveform (e.g., using adaptive filtering) to improve accuracy. Such an approach is described in U.S. patent application Ser. No. 12/559,426 filed Sep. 14, 2009 (entitled "Body-Worn Monitor For Measuring Respiration Rate" and published on Mar. 17, 2011 as U.S. Pub. 2011/0066062), the contents of which are incorporated herein by reference. Furthermore, as shown in FIG. 12B, the baseline of the TBI waveform, called $Z_0$ or alternatively TFI, can be easily determined. $Z_0$ is used to determine SV, as described above in Equation 4.

With the foregoing description of how the sensor 10 operates (computationally speaking) in mind, the circuitry used to generate, sense, and analyze the corresponding signals is easier to understand. Thus, FIG. 13 illustrates an analog circuit 134 that performs impedance measurement according to the invention. The figure shows just one possible embodiment of the circuit 134; similar monitoring results can be achieved using a design and collection of electrical components that differ from those shown in the figure.

The circuit 134 has a first current-injecting electrode region 138a that injects a high-frequency, low-amperage current (I1) into the patient's thoracic cavity. This serves as the current source. Typically, a current pump 140 provides the modulated current, with the modulation frequency typically being between 50 KHz and 100 KHz and the current magnitude being between 0.1 mA and 10 mA. Preferably, the current pump 140 provides current with a magnitude of 4 mA that is modulated at 70 kHz through the first current-injecting electrode region 138a. A second current-injecting electrode region 138b also injects a high-frequency, low-amperage current (I2) into the patient's thoracic cavity, with the current injected by the second current-injecting region 138b being 180° out of phase with respect to the current (I1) injected by the first current-injecting electrode region.

Sensing-electrode regions 142a and 142b sense the time-dependent voltages encountered by the propagating current I1 and I2, respectively. These sensing-electrode regions are indicated in the figure as S1 and S2. Per Ohm's law as indicated above, the voltage sensed by these sensing-electrode regions 142a, 142b divided by the magnitude of the injected current yields a time-dependent resistance (i.e., impedance) that relates to blood flow in the aortic artery. As shown by the waveform 144 in the figure, the time-dependent resistance features a slowly varying DC offset, characterized by $Z_0$, that indicates the baseline impedance encountered by the injected current; for TBI, this will depend, for example, on the amount of thoracic fluids, along with the fat, bone, muscle, and blood volume in the chest of a given patient. $Z_0$, which typically has a value between about 10 and about 150Ω, is also influenced by low-frequency, time-dependent processes such as respiration. Such processes affect the inherent capacitance near the chest region that TBI measures and are manifested in the waveform by low-frequency undulations, such as those shown in the waveform 144. A relatively small (typically about 0.1-0.5Ω) AC component, Z(t) lies on top of $Z_0$ and is attributed to changes in resistance caused by the heartbeat-induced blood that propagates in the brachial artery as described in detail above. Z(t) is processed with a high-pass filter to form a TBI signal that features a collection of individual pulses 146 that are ultimately processed to determine SV and CO as described above.

Voltage signals measured by the first sensing-electrode region 142a (S1) and the second sensing-electrode region 142b (S2) feed into a differential amplifier 148 to form a single, differential voltage signal which is modulated according to the modulation frequency (e.g., 70 kHz) of the current pump 140. From there, the signal flows to a demodulator 150, which also receives a carrier frequency from the current pump 140 to selectively extract signal components that only correspond to the TBI measurement. The collective function of the differential amplifier 148 and the demodulator 150 can be accomplished using many different circuits designed to extract weak signals—such as the TBI signal—from noise. For example, these components can be combined to form something equivalent to a "lock-in amplifier" that selectively amplifies signal components occurring at a well-defined carrier frequency. Or the signal and carrier frequencies can be deconvoluted in much the same manner as that used in a conventional AM radio using a circuit featuring one or more diodes. The phase of the demodulated signal may also be adjusted with a phase-adjusting component 152 during the amplification process. In one embodiment of a sensor according to the invention, the ADS1298 family of chipsets marketed by Texas Instruments may be used for this application. This chipset features fully integrated analog front ends for both ECG and impedance pneumography. The latter measurement is performed with components for digital differential amplification, demodulation, and phase adjustment—such as those used for the TBI measurement—that are integrated directly into the chipset.

Once the TBI signal is extracted, it flows to a series of analog filters 154, 156, 158 within the circuit 134 that remove extraneous noise from the $Z_0$ and $Z(t)$ signals. The first low-pass filter 154 (30 Hz) removes any high-frequency noise components (e.g. power line components at 60 Hz) that may corrupt the signal. "Part" of the signal that passes through the filter 154, which represents $Z_0$, is ported directly to a channel in an analog-to-digital converter 160. The "remaining" part of the signal feeds into a high-pass filter 156 (0.1 Hz), which lets pass high-frequency signal components responsible for the shape of individual TBI pulses 146. This signal then passes through a final low-pass filter 158 (10 Hz) to further remove any high-frequency noise. Finally, the filtered signal passes through a programmable gain amplifier (PGA) 162, which, using a 1.65V reference, amplifies the resultant signal with a computer-controlled gain. The amplified signal represents $Z(t)$ and is ported to a separate channel of the analog-to-digital converter 160, where it is digitized alongside of $Z_0$. The analog-to-digital converter and PGA are integrated directly into the ADS1298 chipset described above. The chipset can simultaneously digitize waveforms such as $Z_0$ and $Z(t)$ with 24-bit resolution and sampling rates (e.g. 500 Hz) that are suitable for physiological waveforms. Thus, in theory, this one chipset can perform the function of the differential amplifier 148, demodulator 150, PGA 162, and analog-to-digital converter 160. Reliance on just a single chipset to perform these multiple functions ultimately reduces both size and power consumption of the TBI circuit 134.

The microprocessor 136 receives digitized $Z_0$ and $Z(t)$ signals through a conventional digital interface such as an SPI or I2C interface. Algorithms for converting the waveforms into actual measurements of SV and CO are performed by the microprocessor 136. The microprocessor 136 also receives digital motion-related waveforms from the on-board accelerometer and processes these waveforms to determine parameters such as the degree/magnitude of motion, frequency of motion, posture, and activity level.

Figure 14:
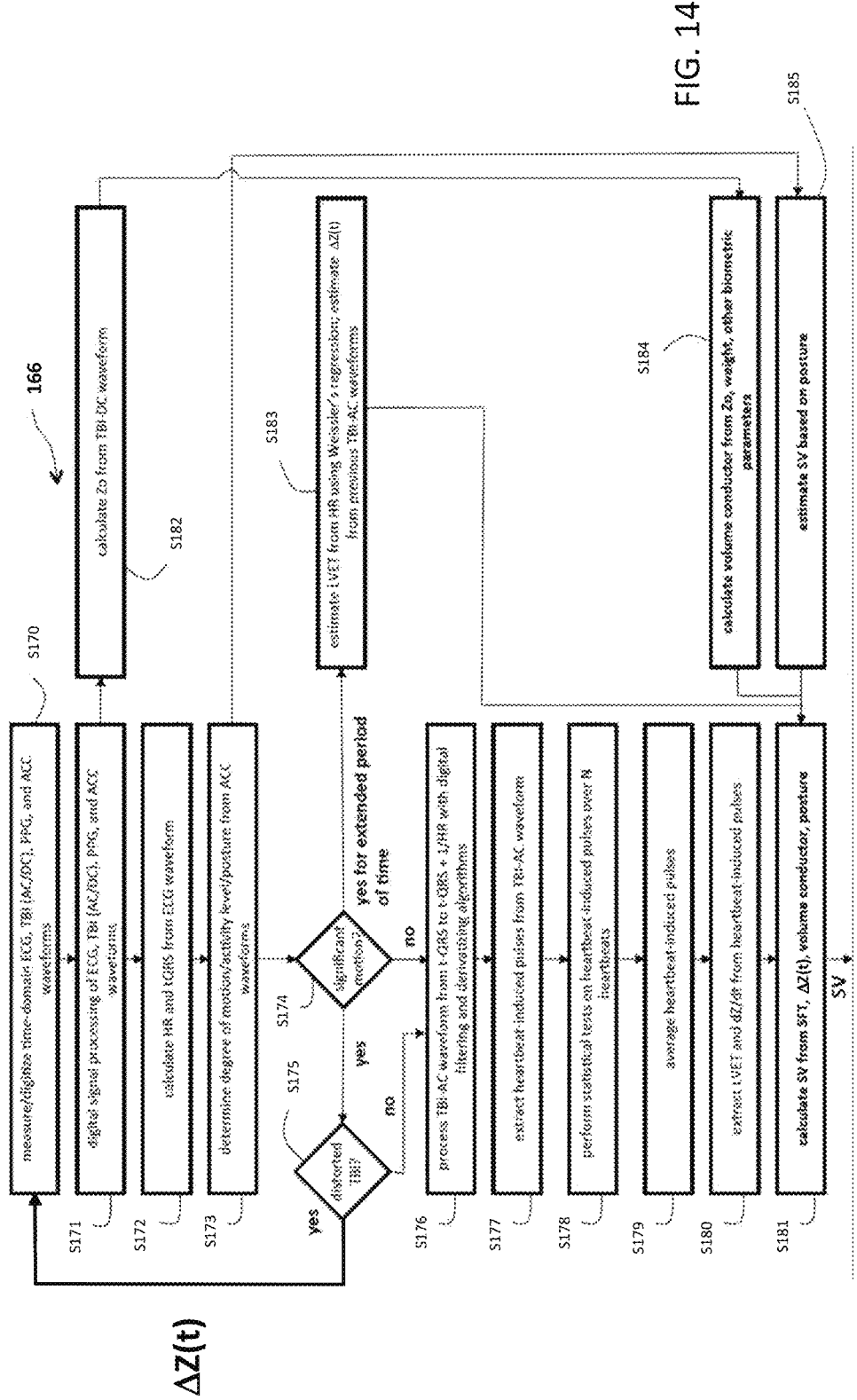
FIG. 14 is a corresponding flow chart illustrating how the sensor measures TBI waveforms and calculates values of SV in the presence of motion.

A corresponding flow chart of an algorithm 166 that functions using compiled computer code operating, e.g., on the onboard microprocessor 136 is shown in FIG. 14. The algorithm 166 is used to measure TBI waveforms and, from them, CO and SV in the presence of motion. The compiled computer code is loaded in memory associated with the microprocessor and is run each time a TBI measurement is converted into numerical values for CO and SV. The microprocessor typically runs an embedded real-time operating system, and the compiled computer code is typically written in a language such as C, C++, Java, or assembly language. Each step S170-S185 in the algorithm 166 is typically carried out by a function or calculation included in the compiled computer code.

Algorithms similar to that shown in FIG. 14 can be used to calculate other physiological parameters in the presence of motion such as SpO2, RR, HR, PR, PTT, and SYS/DIA based on PTT.

Figure 15:
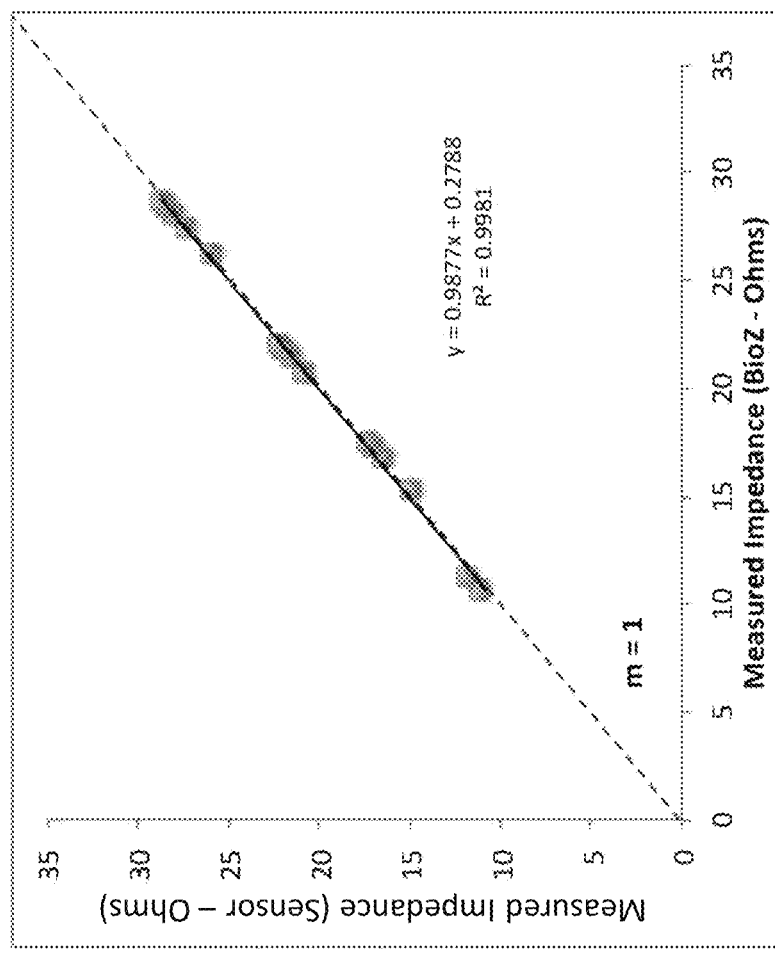
FIG. 15 is a graph showing the correlation of TFI measured by the sensor and a related, impedance-derived parameter measured with a reference device, the BioZ.
Figure 16:
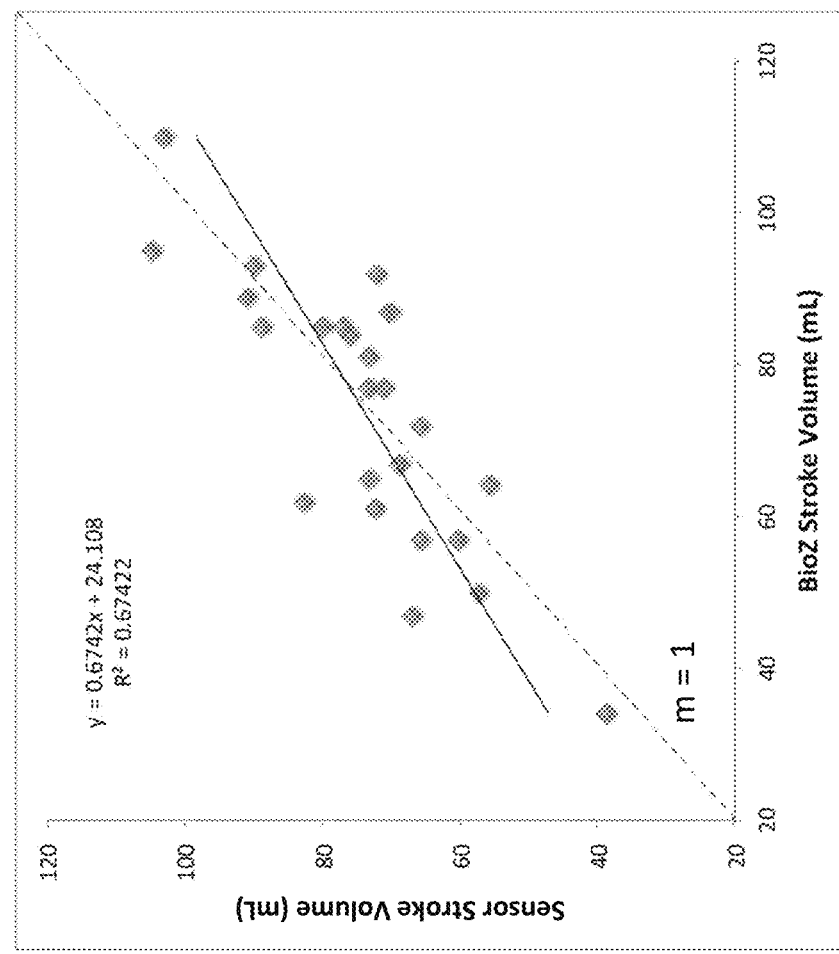
FIG. 16 is a graph showing the correlation of SV measured by the sensor and SV measured with a reference device, the BioZ; and, FIG. 17 is a graph showing the correlation of RR measured by the sensor and RR measured with a reference device, a vital sign monitor with an end-tidal CO2 sensor.
Figure 17:
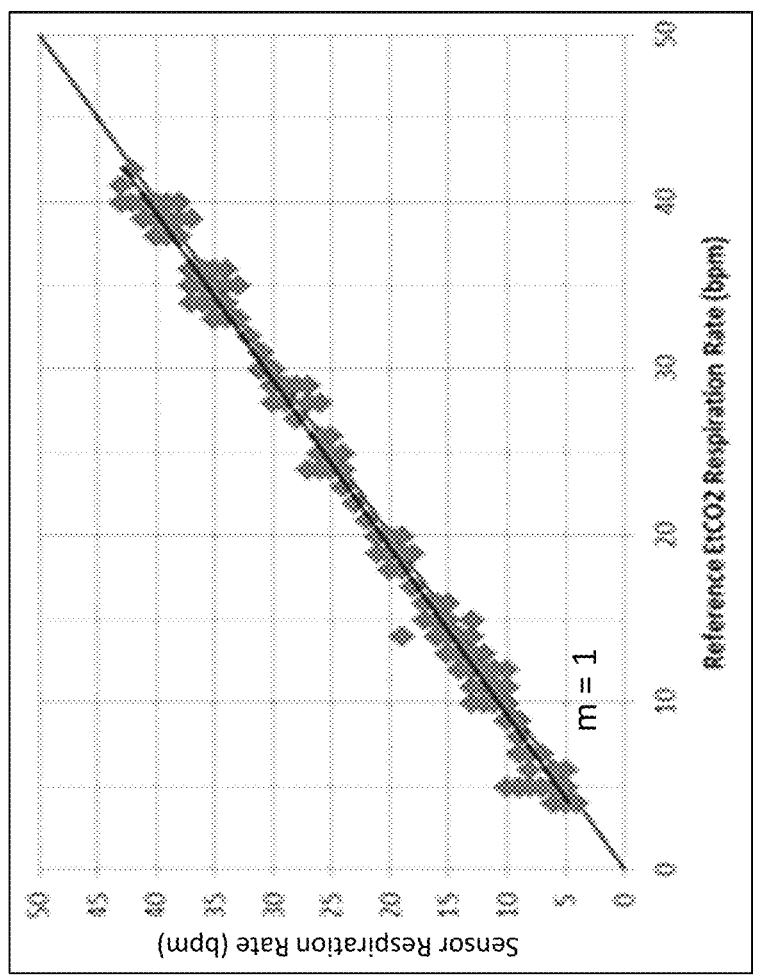

As for accuracy/reliability of the parameters measured and calculated in this manner, FIGS. 15-17 show correlation plots indicating the efficacy of the sensor's measurements of TFI (FIG. 15), SV (FIG. 16), and RR (FIG. 17). In each plot, the value measured by the sensor is shown on the y-axis, and the value measured by a reference device is shown on the x-axis. Perfect correlation is indicated by the line with a slope of m=1 running through the plot. Each data point in the plots represents data from a unique patient, as measured during a clinical trial. For the plots showing TFI and SV, the reference is the Cardiodynamics BioZ, which is a device that uses impedance cardiography to measure corresponding values of $Z_0$. For the plot showing RR, the reference device is a vital sign monitor performing a measurement of end-tidal CO2. As is clear from the figures, the sensor's measurements of its respective parameters correlate strongly with the reference techniques.

Finally, as shown in FIG. 13, both numerical and waveform data processed with the microprocessor 136 are ported to a wireless transmitter 16 such as a transmitter based on protocols like Bluetooth® or 802.11a/b/g/n. From there, the transmitter 16 sends data to an external receiver such as a conventional cellular telephone, tablet, wireless hub (such as Qualcomm's 2Net™ system), or personal computer. Devices like these can serve as a "hub" to forward data to an Internet-connected remote server located, e.g., in a hospital, medical clinic, nursing facility, or eldercare facility, and there a clinician is able to evaluate the data for early markers of CHF, ESRD, or other physiological conditions as well as physical conditions (e.g., fallen, ambulating, etc.), as explained above.

Other embodiments are deemed to be within the scope of the invention. For example, algorithms can process other waveforms, such as the PPG and ECG waveforms, to extract parameters such as RR. In that case, the low-frequency envelope of the waveform indicates RR. In other embodiments, the reflective pulse oximetry system that measures SpO2 can be replaced with an ear-worn optical sensor that connects to the sensor through a cable. Here, the sensor uses either reflective or transmission-mode optical configurations to measure both the red and infrared PPG waveforms. In other embodiments, algorithms that operate on either the sensor or the gateway monitor trends in physiological parameters to determine the onset of a particular disease, e.g. CHF. In still other embodiments, the electronics and mechanical components within the sensor can be relocated within the sensor's geometry. For example, they can be moved from the back portion of the sensor to a side portion proximal to the front of the patient's neck. Still further, the control circuit could be relocated from the clasp assembly to the sensing portion of the sensor.

In other embodiments, the system shown above can take the form of a 'patch' that directly adheres to a portion of a patient's body, as opposed to a 'necklace' that drapes around the patient's neck. The patch would be similar in form to the necklace's base, although it may take on other shapes and form factors. It would include all the same sensors (e.g. sensors for measuring ECG, TBI, and PPG waveforms) and computing systems (e.g. microprocessors operating algorithms for processing these waveforms to determine parameters such as HR, HRV, RR, BP, SpO2, TEMP, CO, SV, fluids) as the base of the necklace. However unlike the system described above, the battery to power the patch would be located in or proximal to the base, as opposed to the strands in the case of the necklace. Also, in embodiments, the patch would include a mechanism such as a button or tab functioning as an on/off switch. Alternatively, the patch would power on when sensors therein (e.g. ECG or temperature sensors) detect that it is attached to a patient.

In typical embodiments, the patch includes a reusable electronics module (shaped, e.g., like the base of the necklace) that snaps into a disposable component that includes electrodes similar to those described above. The patch may also include openings for optical and temperature sensors as described above. In embodiments, for example, the disposable component can be a single disposable component that receives the reusable electronics module. In other embodiments, the reusable electronics module can include a reusable electrode (made, e.g., from a conductive fabric or elastomer), and the disposable component can be a simple adhesive component that adheres the reusable electrode to the patient.

In preferred embodiments the patch is worn on the chest, and thus includes both rigid and flexible circuitry, as described above. In other embodiments, the patch only includes rigid circuitry and is designed to fit on other portions of the patient's body that is more flat (e.g. the shoulder).

Still other embodiments are within the scope of the invention.

What is claimed is:

1. A sensor for measuring from a patient a systolic blood pressure (SYS), a diastolic blood pressure (DIA), and a pulse oximetry (SpO2), the sensor configured to be located on the patient's chest and comprising:

a sensing portion having a flexible housing configured to be located on the patient's chest and enclosing a battery, wireless transmitter, and all of the sensor's sensing and electronic components, including:

at least two pairs of electrode contact points disposed on a bottom surface of the flexible housing, with each pair of electrode contact points comprising a current-injecting electrode contact point and a voltage-sensing electrode contact point;

an analog electrocardiogram (ECG) circuit contained entirely within the flexible housing and in electrical contact with a first voltage-sensing electrode contact point from a first pair of electrode contact points and a second voltage-sensing electrode contact point from a second pair of electrode contact points, the analog ECG circuit configured to generate an analog ECG waveform based on sensed voltage;

an analog impedance circuit contained entirely within the flexible housing and in electrical contact with current-injecting and voltage-sensing electrode contact points in both the first and second pair of electrode contact points, the analog impedance circuit being configured to generate an analog impedance waveform based on sensed voltage;

an optical system located on a bottom surface of the flexible housing, the optical system comprising a light source configured to generate radiation in both the red and infrared spectral ranges that separately irradiates a portion of the patient's chest disposed underneath the flexible housing, and a photodetector configured to detect radiation in the red spectral range that reflects off the portion of the patient's chest to generate a first analog photoplethysmogram waveform (red-PPG), and to detect radiation in the infrared spectral range that reflects off the portion of the patient's chest to generate a second analog photoplethysmogram waveform (infrared-PPG), with the optical system located between a first electrode contact point and a second electrode contact point of one of the two pairs of electrode contact points and configured to be releasably connected to the patient's chest by the electrode contact points, such that the optical system irradiates the portion of the patient's chest between the first electrode contact point and the second electrode contact point of one of the two pairs of electrode contact points;

a digital processing system contained entirely within the housing and comprising a microprocessor and an analog-to-digital converter, the digital processing system being configured to: 1) digitize the analog ECG waveform to generate a digital ECG waveform, 2) digitize the analog impedance waveform to generate a digital impedance waveform, 3) digitize the analog red-PPG waveform to generate a digital red-PPG waveform, and 4) digitize the analog infrared-PPG waveform to generate a digital infrared-PPG waveform;

a first sensor for measuring stroke volume (SV) disposed within the flexible housing, the first sensor comprising a first processor configured to determine SV from a maximum value of a mathematical derivative of the digital impedance waveform and a baseline value of the digital impedance waveform;

a second sensor for measuring blood pressure contained entirely within the flexible housing, the second sensor comprising a second processor configured to collectively process the digital impedance waveform and one of the digital red-PPG and infrared-PPG waveforms to determine: 1) a first time point from one of the digital red-PPG and digital infrared-PPG waveforms, 2) a second time point from the digital impedance waveform, 3) a vascular transit time (VTT) from the temporal difference between the first and second time points, 4) a value of SYS from a linear equation that includes an inverse value of VTT, 5) a value of pulse pressure (PP) from the product of SV and a calibration parameter relating this to PP, and 6) a value of DIA from the mathematical difference between SYS and PP; and a third sensor for measuring SpO2 contained entirely within the flexible housing, the third sensor comprising a third processor configured to determine a value of SpO2 from alternating and static components of both the digital red-PPG waveform and digital infrared-PPG waveform.

2. The sensor of claim 1, wherein the flexible housing comprises two or more rigid housing segments that are connected to each other by means of one or more flexible connectors.

3. The sensor of claim 2, wherein the analog ECG and analog impedance circuits and the digital processing system are located on rigid circuit boards disposed within the housing segments and the analog ECG circuit, analog impedance circuit, and digital processing system are interconnected via one or more flexible conductors located within the one or more flexible connectors.

4. The sensor of claim 3, wherein each of the one or more flexible connectors comprises a flexible circuit.

5. The sensor of claim 4, wherein the analog ECG circuit and the digital processing system are located on separate rigid circuit boards located in separate housing segments.

6. The sensor of claim 4, wherein the analog impedance circuit and the digital processing system are located on separate rigid circuit boards located in separate housing segments.

7. The sensor of claim 4, wherein the housing comprises three rigid housing segments, with the analog ECG circuit, the analog impedance circuit, and the digital processing system each being located in one of the three housing segments.

8. The sensor of claim 7, wherein the digital processing system is located in a middle segment of said three housing segments, with each of the analog ECG circuit and the analog impedance circuit being located in a respective outboard housing segment and being connected to the digital processing system via a respective flexible circuit.

9. The sensor of claim 2, wherein the sensing portion includes first and second pairs of electrode contact points, with 1) the first pair of electrode contact points including a first voltage-sensing electrode contact point that is located in a first housing segment arranged to contact a first side of the patient's chest, and 2) the second pair of electrode contact points including a second voltage-sensing electrode contact point that is located in a second housing segment arranged to contact a second side of the patient's chest that is laterally opposite to the first side of the patient's chest.

10. The sensor of claim 2, wherein the sensing portion includes first and second pairs of electrode contact points, with 1) the first pair of electrode contact points including a first current-injecting electrode contact point that is located in a first housing segment arranged to contact a first side of the patient's chest, and 2) the second pair of electrode contact points including a second current-injecting electrode contact point that is located in a second housing segment arranged to contact a second side of the patient's chest that is laterally opposite to the first side of the patient's chest.

11. The sensor of claim 2, wherein the sensing portion includes first and second pairs of electrode contact points, with 1) the first pair of electrode contact points including a first voltage-sensing electrode contact point and a first current-injecting electrode contact point that are both located in a first housing segment arranged to contact a first side of the patient's chest; and 2) the second pair of electrode contact points including a second voltage-sensing electrode contact point and a second current-injecting electrode contact point that are both located in a second housing segment arranged to contact a second side of the patient's chest that is laterally opposite to the first side of the patient's chest.

12. The sensor of claim 1, wherein the analog ECG circuit and the analog impedance circuit generate the ECG waveform and the impedance waveform, respectively, using the same voltage sensed at the voltage-sensing electrode contact point.

13. The sensor of claim 11, wherein the analog ECG circuit and the analog impedance circuit generate the ECG waveform and the impedance waveform, respectively, using the same voltage sensed at the voltage-sensing electrode contact point, of each pair of electrode contact points, within each of the first and second housing segments.

14. The sensor of claim 1, wherein the light source is configured to generate radiation in the red spectral range near 600 nm.

15. The sensor of claim 1, wherein the light source is configured to generate radiation in the infrared spectral range near 800 nm.

16. The sensor of claim 1, wherein SYS is estimated from the equation:

$$SYS \sim \frac{m_{SYS}}{VTT}$$

where $m_{sys}$ is a patient-specific slope determined during a calibration that relates SYS to VTT.

17. The sensor of claim 1, wherein SV is estimated from the equation $$SV \sim \frac{\left(\frac{dZ(t)}{dt}\right)_{max}}{Z_0}$$

where $(dZ(t)/dt)_{max}$ is the maximum value of a mathematical derivative of the digital impedance waveform and $Z_0$ is the baseline value of the digital impedance waveform.

18. A sensor for measuring from a patient a systolic blood pressure (SYS), a diastolic blood pressure (DIA), and a pulse oximetry (SpO2), the sensor configured to be located on the patient's chest and comprising:
a sensing portion having a flexible housing configured to be located on the patient's chest and enclosing a battery, a wireless transmitter, and all of the sensor's sensing and electronic components, including:
at least two pairs of electrode contact points disposed on a bottom surface of the flexible housing, with each pair of electrode contact points comprising a current-injecting electrode contact point and a voltage-sensing electrode contact point;
an analog electrocardiogram (ECG) circuit contained entirely within the flexible housing and in electrical contact with a first voltage-sensing electrode contact point from a first pair of electrode contact points and a second voltage-sensing electrode contact point from a second pair of electrode contact points, the analog ECG circuit configured to generate an ECG waveform based on sensed voltage;
an analog impedance circuit contained entirely within the flexible housing and in electrical contact with current-injecting and voltage-sensing electrode contact points in both the first and second pair of electrode contact points, the analog impedance circuit being configured to generate an impedance waveform based on sensed voltage;
an optical system located on a bottom surface of the flexible housing, the optical system comprising a light source configured to generate radiation in both the red and infrared spectral ranges that separately irradiates a portion of the patient's chest disposed underneath the flexible housing, and a photodetector configured to detect radiation in the red spectral range that reflects off the portion of the patient's chest to generate a first photoplethysmogram waveform (red-PPG), and to detect radiation in the infrared spectral range that reflects off the portion of the patient's chest to generate a second photoplethysmogram waveform (infrared-PPG), with the optical system located between a first electrode contact point and a second electrode contact point of one of the two pairs of electrode contact points and configured to be releasably connected to the patient's chest by the electrode contact points, such that the optical system irradiates the portion of the patient's chest between the first electrode contact point and the second electrode contact point of one of the two pairs of electrode contact points;

a first sensor for measuring stroke volume (SV) disposed within the flexible housing, the first sensor comprising a first processor configured to determine a value of SV from a maximum value of a mathematical derivative of the impedance waveform and a baseline value of the impedance waveform;

a second sensor for measuring blood pressure contained entirely within the flexible housing, the second sensor comprising a processor configured to collectively processes the impedance waveform and one of the red-PPG and infrared-PPG waveforms to determine: 1) a first time point from one of the red-PPG and infrared-PPG waveforms, 2) a second time point from the impedance waveform, 3) a vascular transit time (VTT) from the temporal difference between the first and second time points, 4) a value of SYS from a linear equation that includes an inverse value of VTT, 5) a value of pulse pressure (PP) from the product of SV and a calibration parameter relating SV and PP, and 6) a value of DIA from the mathematical difference between SYS and PP; and a third sensor for measuring SpO2 contained entirely within the flexible housing, the third sensor comprising a processor configured to determine a value of SpO2 from alternating and static components of both the digital red-PPG waveform and digital infrared-PPG waveform.

* * * * *